United States Patent [19]
Anderson et al.

[11] Patent Number: 5,094,953
[45] Date of Patent: Mar. 10, 1992

[54] HUMAN TISSUE PLASMINOGEN ACTIVATOR VARIANTS

[75] Inventors: Stephen P. Anderson; Deborah L. Higgins, both of San Mateo; Adair J. Hotchkiss, Half Moon Bay; Cara B. Marks, San Francisco, all of Calif.

[73] Assignee: Genentech, Inc., South San Francisco, Calif.

[21] Appl. No.: 170,510

[22] Filed: Mar. 21, 1988

[51] Int. Cl.$^5$ .................. C12N 9/64; C12N 15/00; C12N 15/58
[52] U.S. Cl. .................. 435/226; 435/172.3; 435/212; 935/27; 935/56; 536/27
[58] Field of Search .......... 435/212, 69.1, 226, 435/172.3; 935/27, 56; 536/27

[56] References Cited

U.S. PATENT DOCUMENTS 4,935,237 6/1990 Higgins et al. .................. 429/94.64

FOREIGN PATENT DOCUMENTS 0227462 7/1987 European Pat. Off. .
0234051 9/1987 European Pat. Off. .
87/04722 8/1987 PCT Int'l Appl. .

OTHER PUBLICATIONS

Harris, Protein Engineering, vol. 1, pp. 449-458, 1987.
van Zonneveld et al., J. Biol. Chem., vol. 261, No. 30, pp. 14214-14218, Oct. 25, 1986.
Zoller et al., Methods in Enzymology, vol. 154 Part E, pp. 329-350, 1987.
Tate et al., Biochemistry 26 (2), 338-343 (1987).
Higgins et al., Thrombosis and Heamostasis 58 (1), 287 (1987) Abstract 1043.
Kagitani et al., Febs Letters 189 (1), 145-149 (1985).

Primary Examiner—Richard A. Schwartz
Assistant Examiner—Nancy Treptow
Attorney, Agent, or Firm—Walter H. Dreger

[57] ABSTRACT

Disclosed are novel variants of tissue plasminogen activator (t-PA) that have surprising biological/pharmacokinetic properties compared with native t-PA. For example, certain of the variants hereof demonstrate increased half-life profiles, and show good fibrin binding activity even though fibrin binding regions of the molecule are deleted. All associated means and methods for preparing such variants recombinantly and for using such variants are also disclosed.

3 Claims, 21 Drawing Sheets

Fig.9-1.

```
              -30                                          -20
     MetAspAlaMetLysArgGlyLeuCysCysValLeuLeuLeuCysGlyAlaValPheVal
  1  ATGGATGCAATGAAGAGAGGGCTCTGCTGTGTGCTGCTGCTGTGTGGAGCAGTCTTCGTT

-10                                          -1  45
     SerProSerGlnGluIleHisAlaArgPheArgArgGlyAlaArgSerValProValLys
     TCGCCCAGCCAGGAAATCCATGCCCGATTCAGAAGAGGAGCCAGATCTGTGCCTGTCAAA 50                                           60
     SerCysSerGluProArgCysPheAsnGlyGlyThrCysGlnGlnAlaLeuTyrPheSer
 121 AGTTGCAGCGAGCCAAGGTGTTTCAACGGGGGCACCTGCCAGCAGGCCCTGTACTTCTCA 70                                           80
     AspPheValCysGlnCysProGluGlyPheAlaGlyLysCysCysGluIleAspThrArg
     GATTTCGTGTGCCAGTGCCCCGAAGGATTTGCTGGGAAGTGCTGTGAAATAGATACCAGG 90                                           100
     AlaThrCysTyrGluAspGlnGlyIleSerTyrArgGlyThrTrpSerThrAlaGluSer
 241 GCCACGTGCTACGAGGACCAGGGCATCAGCTACAGGGGCACGTGGAGCACAGCGGAGAGT 110                                          120
     GlyAlaGluCysThrAsnTrpAsnSerSerAlaLeuAlaGlnLysProTyrSerGlyArg
     GGCGCCGAGTGCACCAACTGGAACAGCAGCGCGTTGGCCCAGAAGCCCTACAGCGGGCGG 130                                          140
     ArgProAspAlaIleArgLeuGlyLeuGlyAsnHisAsnTyrCysArgAsnProAspArg
 361 AGGCCAGACGCCATCAGGCTGGGCCTGGGGAACCACAACTACTGCAGAAACCCAGATCGA
```

Fig. 9-2.

```
                150                                          160
      AspSerLysProTrpCysTyrValPheLysAlaGlyLysTyrSerSerGluPheCysSer
      GACTCAAAGCCCTGGTGCTACGTCTTTAAGGCGGGGAAGTACAGCTCAGAGTTCTGCAGC 170                                          180
      ThrProAlaCysSerGluGlyAsnSerAspCysTyrPheGlyAsnGlySerAlaTyrArg
  481 ACCCCTGCCTGCTCTGAGGGAAACAGTGACTGCTACTTTGGGAATGGGTCAGCCTACCGT 190                                          200
      GlyThrHisSerLeuThrGluSerGlyAlaSerCysLeuProTrpAsnSerMetIleLeu
      GGCACGCACAGCCTCACCGAGTCGGGTGCCTCCTGCCTCCCGTGGAATTCCATGATCCTG 210                                          220
      IleGlyLysValTyrThrAlaGlnAsnProSerAlaGlnAlaLeuGlyLeuGlyLysHis
  601 ATAGGCAAGGTTTACACAGCACAGAACCCCAGTGCCCAGGCACTGGGCCTGGGCAAACAT 230                                          240
      AsnTyrCysArgAsnProAspGlyAspAlaLysProTrpCysHisValLeuLysAsnArg
      AATTACTGCCGGAATCCTGATGGGGATGCCAAGCCCTGGTGCCACGTGCTGAAGAACCGC 250                                          260
      ArgLeuThrTrpGluTyrCysAspValProSerCysSerThrCysGlyLeuArgGlnTyr
  721 AGGCTGACGTGGGAGTACTGTGATGTGCCCTCCTGCTCCACCTGCGGCCTGAGACAGTAC 270                                          280
      SerGlnProGlnPheGluIleLysGlyGlyLeuPheAlaAspIleAlaSerHisProTrp
      AGCCAGCCTCAGTTTGAAATCAAAGGAGGGCTCTTCGCCGACATCGCCTCCCACCCCTGG 290                                          300
      GlnAlaAlaIlePheAlaLysHisArgArgSerProGlyGluArgPheLeuCysGlyGly
  841 CAGGCTGCCATCTTTGCCAAGCACAGGAGGTCGCCCGGAGAGCGGTTCCTGTGCGGGGGC
```

Fig. 9-3.

```
     310                             320
IleLeuIleSerSerCysTrpIleLeuSerAlaAlaHisCysPheGlnGluArgPhePro
ATACTCATCAGCTCCTGCTGGATTCTCTCTGCCGCCCACTGCTTCCAGGAGAGGTTTCCG 330                             340
ProHisHisLeuThrValIleLeuGlyArgThrTyrArgValValProGlyGluGluGlu
961  CCCCACCACCTGACGGTGATCTTGGGCAGAACATACCGGGTGGTCCCTGGCGAGGAGGAG 350                             360
GlnLysPheGluValGluLysTyrIleValHisLysGluPheAspAspAspThrTyrAsp
     CAGAAATTTGAAGTCGAAAAATACATTGTCCATAAGGAATTCGATGATGACACTTACGAC 370                             380
AsnAspIleAlaLeuLeuGlnLeuLysSerAspSerSerArgCysAlaGlnGluSerSer
1081 AATGACATTGCGCTGCTGCAGCTGAAATCGGATTCGTCCCGCTGTGCCCAGGAGAGCAGC 390                             400
ValValArgThrValCysLeuProProAlaAspLeuGlnLeuProAspTrpThrGluCys
     GTGGTCCGCACTGTGTGCCTTCCCCCGGCGGACCTGCAGCTGCCGGACTGGACGGAGTGT 410                             420
GluLeuSerGlyTyrGlyLysHisGluAlaLeuSerProPheTyrSerGluArgLeuLys
1201 GAGCTCTCCGGCTACGGCAAGCATGAGGCCTTGTCTCCTTTCTATTCGGAGCGGCTGAAG 430                             440
GluAlaHisValArgLeuTyrProSerSerArgCysThrSerGlnHisLeuLeuAsnArg
     GAGGCTCATGTCAGACTGTACCCATCCAGCCGCTGCACATCACAACATTTACTTAACAGA
```

Fig. 9-4.

```
         450                         460
     ThrValThrAspAsnMetLeuCysAlaGlyAspThrArgSerGlyGlyProGlnAlaAsn
1321 ACAGTCACCGACAACATGCTGTGTGCTGGAGACACTCGGAGCGGCGGGCCCCAGGCAAAC 470                         480
     LeuHisAspAlaCysGlnGlyAspSerGlyGlyProLeuValCysLeuAsnAspGlyArg
     TTGCACGACGCCTGCCAGGGCGATTCGGGAGGCCCCCTGGTGTGTCTGAACGATGGCCGC 490                         500
     MetThrLeuValGlyIleIleSerTrpGlyLeuGlyCysGlyGlnLysAspValProGly
1441 ATGACTTTGGTGGGCATCATCAGCTGGGGCCTGGGCTGTGGACAGAAGGATGTCCCGGGT 510                         520
     ValTyrThrLysValThrAsnTyrLeuAspTrpIleArgAspAsnMetArgProOP#
     GTGTACACAAAGGTTACCAACTACCTAGACTGGATTCGTGACAACATGCGACCGTGA
```

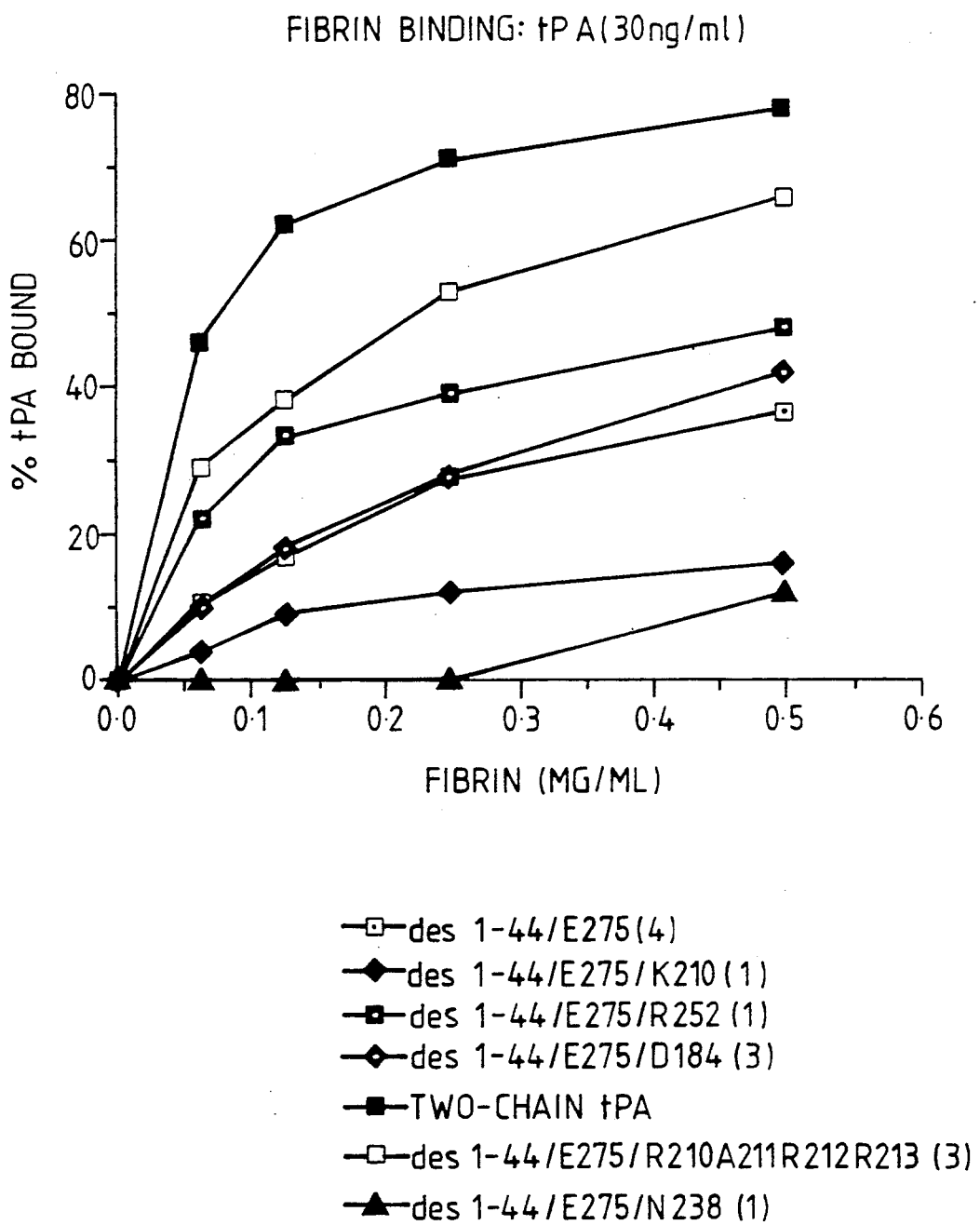

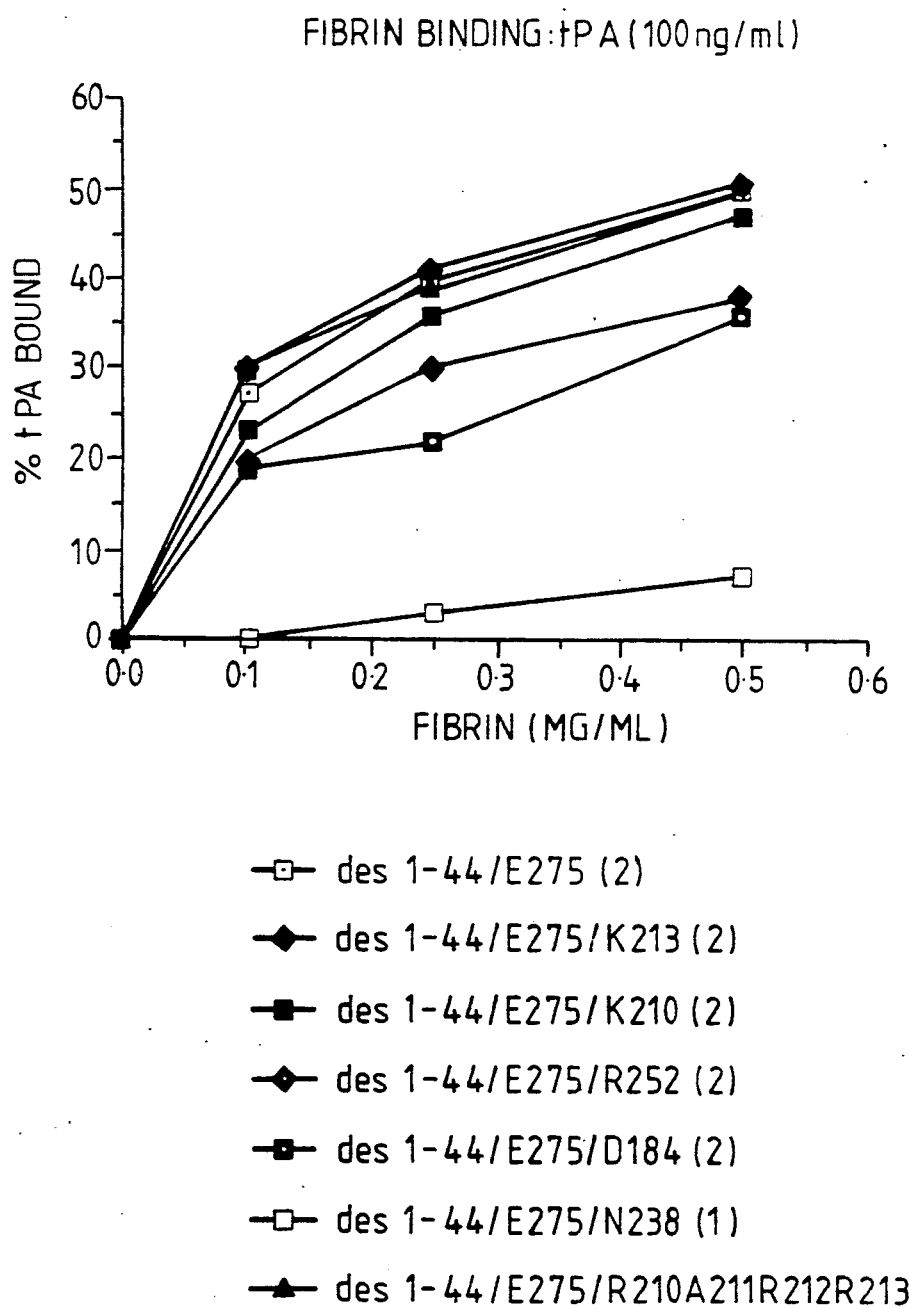

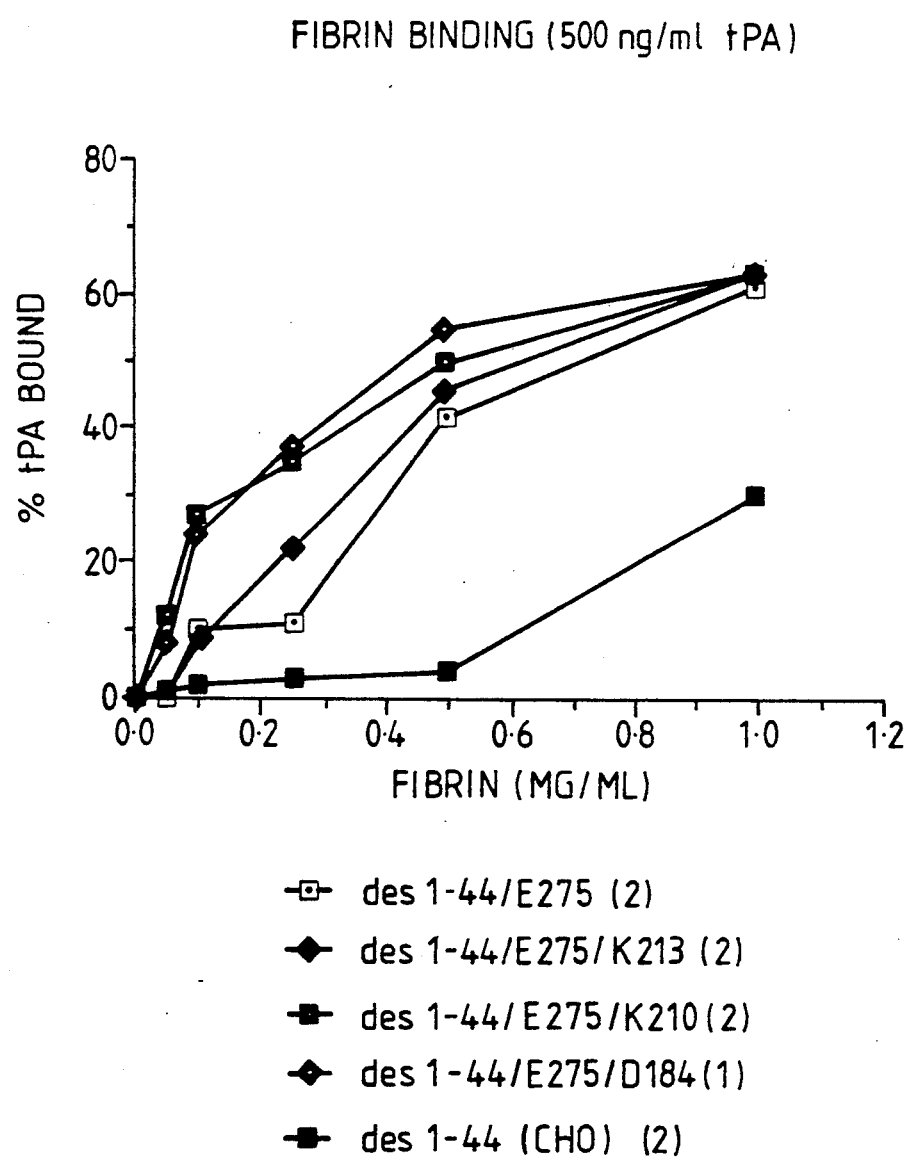

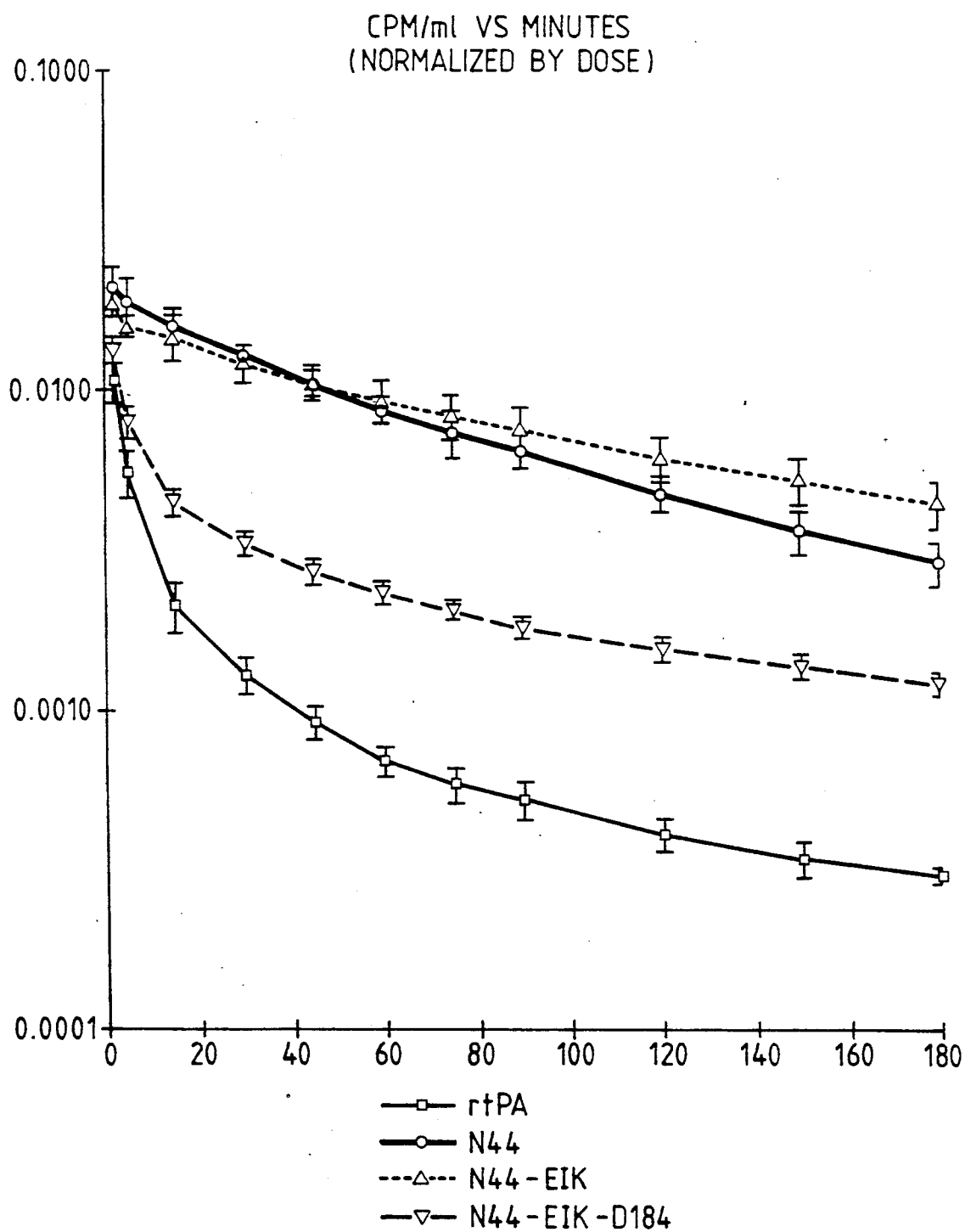

HUMAN TISSUE PLASMINOGEN ACTIVATOR VARIANTS

Reference is made to the following copending patent applications, which are hereby incorporated by reference: 1) U.S. Ser. No. 07/068,448 filed June 30, 1987, now U.S. Pat. No. 4,935,237; 2) U.S. Ser. No. 07/552,480, filed May 11, 1990, and its parent applications U.S. Ser. No. 07/071,506, filed July 9, 1987, Ser. No. 06/846,697. filed Apr. 1, 1986 and Ser. No. 06/725,468, filed Apr. 22, 1985 (corresponding to European Patent Application Publication No. 199,574, published Oct. 29, 1986); and 3) U.S. Ser. No. 07/118,098, filed Nov. 6, 1987, and its parent applications Ser. No. 07/021,893, filed Mar. 4, 1987 and Ser. No. 06/841,075, filed Mar. 18, 1986 (corresponding to European Patent Application Publication No. 238,304, published Sept. 23, 1987).

FIELD OF THE INVENTION

The present invention is directed to particular novel variants of human tissue plasminogen activator (t-PA), to methods for preparing such and to methods and compositions utilizing such variants for producing pharmaceutically active principals with unexpectedly improved pharmacokinetic and pharmacological characteristics and to methods for modulating the pharmacokinetic and pharmacological characteristics of t-PA and various variants thereof. The present invention is more particularly directed to means and methods for modulating fibrin binding of t-PA, and most preferably to increasing fibrin binding in cases where it may have been found suppressed consequential to certain modifications in other domains of the t-PA entity.

BACKGROUND OF THE INVENTION

Human tissue plasminogen activator has been identified and described as a particularly important and potent new biological pharmaceutical agent that has shown extraordinary results in the treatment of vascular diseases, such as myocardial infarction, due to its high fibrin specificity and potent ability to dissolve blood clots in vivo.

Human tissue plasminogen activator has been the subject of numerous scientific and patent application disclosures. Although its existence prompted numerous investigations by several scientific groups, it was first identified as a substantially pure isolate from a natural source, and tested for requisite plasminogen activator activity in vivo. by Collen et al., European Patent Application Publn. No. 41766, published Dec. 16, 1981, based upon a first filing of June 11, 1980. See also the corresponding scientific publication is Rijken et al., *J. Biol. Chem.* 256, 7035 (1981).

Subsequently, human tissue plasminogen activator was fully identified and characterized by underlying DNA sequence and deduced amino acid sequence based on successful work employing recombinant DNA technology resulting in large quantities of t-PA in a distinct milieu. This work was recorded in the scientific literature (Pennica et al., *Nature* 301, 214 (1983)) and in European Patent Application Publn. No. 93619, published Nov. 9, 1983, based upon a first filing of May 5, 1982.

Using the latter disclosure as a basic tool, numerous other researchers have reported on the thus enabled preparation of the molecule via recombinant DNA technology. Certain of these researchers also have publicly disclosed the potential of variants of the basic structure, mentally foreseeing derivatives that may vary in overall biological or pharmacokinetic effects. The resultant public disclosures for the most part have been prophetic and equivocal in terms of actual overall biological or pharmacological results.

Analogous endeavors in the laboratories that succeeded first in producing t-PA recombinantly have been recorded factually in terms of confirmed molecule characterization and observed biological effect, both in the scientific literature and in various patent applications, notably those cited and incorporated herein by reference via the text of the opening paragraph of this application. In all events, the trend seems to favor research along lines of endeavoring to modify the basic structure of human tissue plasminogen activator in order to fully explore and exploit its commercial potential according to various biologically based endpoints.

Based partly upon such research and disclosures, it seems now clear that the human tissue plasminogen activator molecule contains five domains (stretches of amino acid sequence) that have been defined with reference to homologous or otherwise similar structures identified in various other proteins such as trypsin, chymotrypsin, plasminogen, prothrombin, fibronectin and epidermal growth factor. These domains have been designated, starting at the N-terminus of the amino acid sequence of human tissue plasminogen activator, as 1) the finger region (F) that has variously been defined as including amino acid 1 upwards of about 44, 2) the growth factor region (G) that has been variously been defined as stretching from about amino acid 45 upwards of amino acid 91 (based upon its homology with EGF), 3) kringle one (K1) that has been defined as stretching from about amino acid 92 to about 173, 4) kringle two (K2) that has been defined as stretching from about amino acid 180 to about amino acid 261 and 5) the so-called serine protease domain (P) that generally has been defined as stretching from about amino acid 264 to the C-terminal end of the molecule. These domains are situated contiguously generally of one another, or are separated by short "linker" regions, and account for the entire amino acid sequence of from 1 to 527 amino acids in its putative mature form.

Each domain has been described variously as contributing certain specific activity: that is, the finger domain has been variously described as containing a sequence essential or at least of major importance for high binding affinity to fibrin. (This activity is thought important for the high specificity human tissue plasminogen activator displays with respect to clot lysis at the locus of a fibrin rich thrombus.) The growth factor-like region likewise has been associated with cell surface binding activity, at least with respect to urokinase. The Kringle 2 region has also been strongly associated with fibrin binding and with the ability of fibrin to stimulate the activity of t-PA. The serine protease domain seems to enjoy unanimous agreement of being the workhorse domain of the molecule in respect of plasminogen activating activity.

Again, it is noted that the finger region has been generally regarded as spanning amino acids 1.44 of the N-terminus and various researchers have endeavored to produce mutants or variants deleting or partially deleting segments of this domain. Reference is again made to co-pending application Ser. No. 07/068,448, filed June 30, 1987, in this regard.

N-linked glycosylation sites exist in the molecule at amino acid positions 117, 184, 218 and amino acid 448. The site at amino acid 218 is not glycosylated. The glycosylation site at amino acid 117 has been characterized as being a high mannose type, while the other two sites display so-called complex oligosaccharide structures. Sites 117 and 448 seem always to be glycosylated, when the molecule is derived from a host cell capable of effecting glycosylation, while site 184 is thought to be glycosylated in about 50 percent of the molecules. The latter 184 glycosylated/unglycosylated phenomenon has been demonstrated via SDS-PAGE analysis where two bands can be seen, one associated with 184 glycosylated molecules and the other 184 unglycosylated molecules: so-called Type I and Type II t-PA. This partial glycosylation pattern may be the result of site 184 being situated in a conformationally sheltered position between the two kringle structures. For a more detailed discussion of the glycosylation structures of t-PA, reference again is had to co-pending Ser. No. 07/118,098, filed Nov. 6, 1987, and its parents.

A third locus that has received scientific attention is the so-called proteolytic cleavage site within the region defined by amino acids 275 to about 279, and more particularly, the bond between amino acid 275 and 276 of the native molecule. Again, reference is made, in this respect, to co-pending Ser. No. 07/071,506, filed July, 9, 1987, and its parents. Mutagenesis at this site so as to make it less susceptible to proteolytic degradation creates a molecule that remains in a single-, or one-chain, form that is thought to have certain advantages biologically and commercially.

All of these defined domains, glycosylation sites and one-chain/two-chain cleavage site have been described and defined as having specific potential biological activity components. For example, removal of a substantial portion or all of the finger domain results in a molecule with substantially diminished fibrin binding characteristics, albeit in return there is a decrease in the overall rate of clearance of the resultant entity—see Ser. No. 07/068,448.

Modification of the native molecule so as to destroy the one-chain to two-chain cleavage site, as such, results in a molecule with somewhat altered biological activity and more stability while the fibrin binding and fibrin stimulation are increased relative to two-chain t-PA— see Ser. No. 07/071,506.

Alteration of the glycosylation sites, and in particular at amino acid 117, seems invariably to result in a molecule having affected solubility characteristics, that may result additionally in an altered $T_{\frac{1}{2}}$life pattern and/or fibrin binding characteristics see Ser. No. 07/118,098.

Given that high fibrin specificity and binding characteristics are desirable results to be possessed by human tissue plasminogen activator, and in particular, variously altered derivatives or variants thereof (See, for example, European Patent Application Publication No. 234,051, published Sept. 2, 1987), the art serves to teach away from altering the finger region, dramatically decreased clearance rates—See U.S. Ser. No. 07/068,448 cited supra. And yet, given the commercial significance of fibrin binding and fibrin specificity, it is a perceived goal among researchers to produce variants or derivatives of human plasminogen activator that would have high fibrin binding activity without altering the other desirable biological and pharmacokinetic properties otherwise associated with the native material. However, the research path for producing such variants or derivatives of human plasminogen activator is not altogether clear from the art extant. See, for example, European Patent Application Publication No. 231,624, published Aug. 12, 1987.

The uncertainty as to whether and where to alter the t-PA native molecule for perceived improved fibrinolytic properties is particularly emphasized by a relatively recent patent publication identified as WO 87/04722 (published Aug. 13, 1987). This document reflects an elaborate paper mosaic of potential variants of t-PA. Although the publication refers to three regions, namely the amino N-terminus, glycosylation sites and single chain cleavage site, there is no evidence of actual preparation of t-PA species, and no bioactivity or other data; hence, the publication merely "contemplated" that the proteins possess improved fibrinolytic profiles relative to native human t-PA without specific reference as to what is meant by that, either qualitatively or quantitatively. Indeed, many of the variants arguably generically embraced may have lower fibrinolytic activity. As such, it serves at best as a relatively complex mosaic from which one may be invited to experiment; not more.

SUMMARY OF THE INVENTION

A fundamental object of the present invention is the preparation, identification and characterization of t-PA variants having modulated fibrin binding activity and to methods and means to effect same. In its most preferred embodiments, the object hereof is directed to engineering increased fibrin binding to t-PA variants via domains herein identified as responsible for such fibrin binding, and particularly for t-PA variants that may have less fibrin binding, compared with native t-PA, caused by different modifications in the t-PA molecule for purposes of enhancing (an)other characteristic(s) relevant to overall fibrinolytic activity such as $T_{\frac{1}{2}}$-life and/or clearance rate.

The present invention is thus directed to t-PA variants having modulated fibrin binding and to all recombinant means associated with their preparation, for example, DNA isolates encoding same, DNA hybridizing with such isolates, cloning vectors harboring such DNA, operable expression vectors thereof, hosts transfected with such vectors, cultures thus capable of producing the t-PA variants, notably as expression products secreted into the surrounding medium, and to the processes involved in accomplishing all of the above. The present invention is also directed to pharmaceutical compositions comprising effective amounts of such t-PA variants and to methods of administration of such compositions to humans The present invention is also directed to various methods employing the t-PA variants hereof. In one such embodiment there is provided a method for the treatment of vascular disease in a patient comprising preparing a human t-PA variant which exhibits modulated fibrin binding relative to native t-PA, preparing a pharmaceutically acceptable composition which includes said t-PA variant in therapeutically effective concentrations and administering said composition to the patient.

In another such embodiment, there is provided a method for providing a variant human t-PA protein exhibiting modulated fibrin binding relative to native t-PA, the method comprising obtaining a t-PA variant comprising a modified t-PA, comparing the fibrin binding of said variant to that of native t-PA and selecting a variant t-PA so obtained which exhibits a modulated fibrin binding relative to native t-PA.

In overall effect, the present invention restores fibrin binding and fibrin stimulation, a desirable characteristic unique to native t-PA as a fibrinolytic agent and in particular where that characteristic was found to be lacking as a result of modifying native t-PA in other respects in order to impart (an)other desirable characteristic(s). Thus, for example, removal of all or part of the finger domain and/or growth domain and/or kringle 1 domain results in variants having for example the desirable characteristic of increased T½-life and decreased clearance rate, relative to native t-PA. However, these variants consequently have reduced fibrin binding properties, a characteristic substantially essential to the unique t-PA fibrinolytic activity. The present invention in one aspect restores the latter thus providing variants with overall enhanced properties relative to native t-PA, for example, fibrin binding properties akin to native t-PA and increased T½-life/decreased clearance rate relative to native t-PA.

DESCRIPTION OF PARTICULARLY PREFERRED EMBODIMENTS

The present invention is based inter alia upon specific successful research that demonstrates that major alterations in the finger domain, itself substantially diminishing fibrin binding activity, coupled with molecular alterations of the 184 glycosylation site, the one-chain to two-chain cleavage site and/or the Kringle 2 putative lysine binding site results in variants of human plasminogen activator that surprisingly retain the basic biological and pharmacological properties or characteristics of native tissue plasminogen activator, and include the substantial restoration of high fibrin binding properties. The results are molecules that, although differing substantially from native material in overall amino acid sequence, retain its desirable fibrinolytic characteristics in kind and to a degree permitting their exploitation in the commercial sector competitive with native material.

In accord with this embodiment, there is provided human plasminogen activator variants devoid of at least a portion of the finger domain, devoid of glycosylation potential at the glycosylation site surrounding amino acid 184 and having resistance to proteolytic cleavage at the site surrounding amino acids 275 and 276 and/or having amino acid modifications in the putative lysine binding site of Kringle 2. Specifically, this embodiment is manifest by novel t-PA variant species: for example, a molecule devoid of amino acids 1 to 44 (designated des 1-44), optionally having aspartic acid at position 184 (designated D184) and having glutamic acid as position 275 (designated E275), said species having therefore the overall designation by shorthand herein of des 1-44D184E275 t-PA and des 1-44E275 t-PA, and for example, a molecule devoid of amino acids 1.44 (designated des 1-44) and having glutamic acid at position 275 and having RARR at amino acid positions 210-3, designated herein as des 1-44R210A211R212R213E275 t-PA.

For purposes of such shorthand designation of t-PA variants hereof, it is noted that numbers refer to the amino acid residue/position along the 527 amino acid sequence of putative mature t-PA—EPA 093619. Amino acid identification uses the single letter alphabet of amino acids, i.e.:

| Asp | D | Aspartic acid |
|---|---|---|
| Thr | T | Threonine |
| Ser | S | Serine |
| Glu | E | Glutamic acid |
| Pro | P | Proline |
| Gly | G | Glycine |
| Ala | A | Alanine |
| Cys | C | Cysteine |
| Val | V | Valine |
| Met | M | Methionine |
| Ile | I | Isoleucine |
| Leu | L | Leucine |
| Tyr | Y | Tyrosine |
| Phe | F | Phenylalanine |
| His | H | Histidine |
| Lys | K | Lysine |
| Arg | R | Arginine |
| Trp | W | Tryptophan |
| Gln | Q | Glutamine |
| Asn | N | Asparagine | and the number following such single letters refers to the amino acid position, e.g., D184 means a variant having, inter alia an aspartic acid at position 184.

Additional particularly preferred embodiments hereof include t-PA variants devoid of at least a portion of the finger domain, for example, des 1-44, and/or being resistant to cleavage at the 275/6 cleavage site by imposed modifications in the 275 to 279 amino acid region, for example E275 and E275I277 and therefore, for further examples, des 1-44E275, des 1-44E275I277 and all of the above being optionally modified in various other regions of the molecule, for example:

1. Kringle 2 modifications, for example in the region of amino acids about 205-215, especially 210-3, and/or
2. Amino acids about 244-255, especially 252 or its site, and/or
3. Amino acids about 233-242, especially 236-8, and/or
4. Known or newly introduced glycosylation sites, for example amino acid 184, and/or
5. Other modifications resulting in t-PA variants identifiable by increased fibrin binding relative to native t-PA or a variant thereof exhibiting decreased fibrin binding compared with native t-PA but having some other enhanced biological characteristic that remains unaffected in principle.

Particular embodiments of the above-noted variants are:

des 1-44E275 t-PA
des 1-44D184E275 t-PA
des 1-44S184E275 t-PA
des 1-44K213E275 t-PA
des 1-44R210A211R212R213E275 t-PA (a particularly preferred species—see above)
des 1-44R252E275 t-PA
des 1-44K210E275 t-PA
des 1-44R210H211Q212K213E275 t-PA and all of the above additionally having the I277 modification, and combinations and permutations thereof, for example, des 1-44R212R252E275 t-PA, etc.

Additional embodiments include t-PA variants, with or without an intact (portion of) finger domain (for example, amino acids 1-44), and/or with a deleted (or partially) growth factor domain (for example, des about 44-84) and/or a deleted (or partially) Kringle 1 domain (for example, des about 92-179), and/or a deleted (or partially) Kringle 2 domain (for example, des about 174-261) all of which may significantly alter clearance rates relative to native t-PA, all of the above combined with the abovementioned preferred variants, for example, E275, E275I277, Q275I277, etc. In addition, fibrin binding of t-PA can be modulated, most preferably restored or increased, by appropriate substitutions of positively- or negatively-charged amino acid residues on the opposite edges of the putative ligand binding pocket of t-PA.

Thus, also preferred herein are the following variants:

des 1-44D184R210A211R212R213R252E275 t-PA
des 92-179D184R210A211R212R213R252E275 t-PA
des 44-84D184R210A211R212R213R252E275 t-PA
or the N184 and S184 analogous thereof.

BRIEF DESCRIPTION OF THE DRAWINGS

FIG. 9 (parts 1-4) shows the sequence of the des 1-44E275 t-PA mutant encoded by plasmid p1179.

FIG. 12 shows fibrin binding of the following molecules at a t-PA concentration of 30 ng/ml: two-chain native t-PA, des 1-44E275, des 1-44K210E275, des 1-44R252E275, des 1D184E275, des 1-44N238E275, des 1-44R210A211R212R213E275. Results show averages of several independent observations (number of times in parentheses). (All but native expressed transiently in 293 cells.)

FIG. 13 shows fibrin binding of the following molecules at a t-PA concentration of 100 ng/ml: des 1-4-4E275, des 1-44K210E275, des 1-4K213E275, des 1R252E275, des 1-44D184E275, des 1-44N238E275, des 1-44R210A211R212R213E275. Results show averages of several independent observations (number of times in parentheses). (All were from material expressed transiently in 293 cells.)

FIG. 14 shows fibrin binding of the following molecules at a t-PA concentration of 500 ng/ml: two-chain des 1-44, des 1-44E275, des 1-44K210E275, des 1-44K213E275, des 1-44D184E275. Results show averages of several independent observations (number of times in parentheses). (All but native and des 1-44 were from material expressed transiently in 293 cells.)

FIG. 18 shows the pharmacokinetic profiles, in rabbits, of the following molecules (all produced in stable CHO cell lines): native t-PA ("rt-PA"), des 1-44 ("N44"), des 1-44E275 ("N44-EIK"), des 1-44D1-84E275 ("N44-EIL-D184").

DETAILED DESCRIPTION

Figure 1:
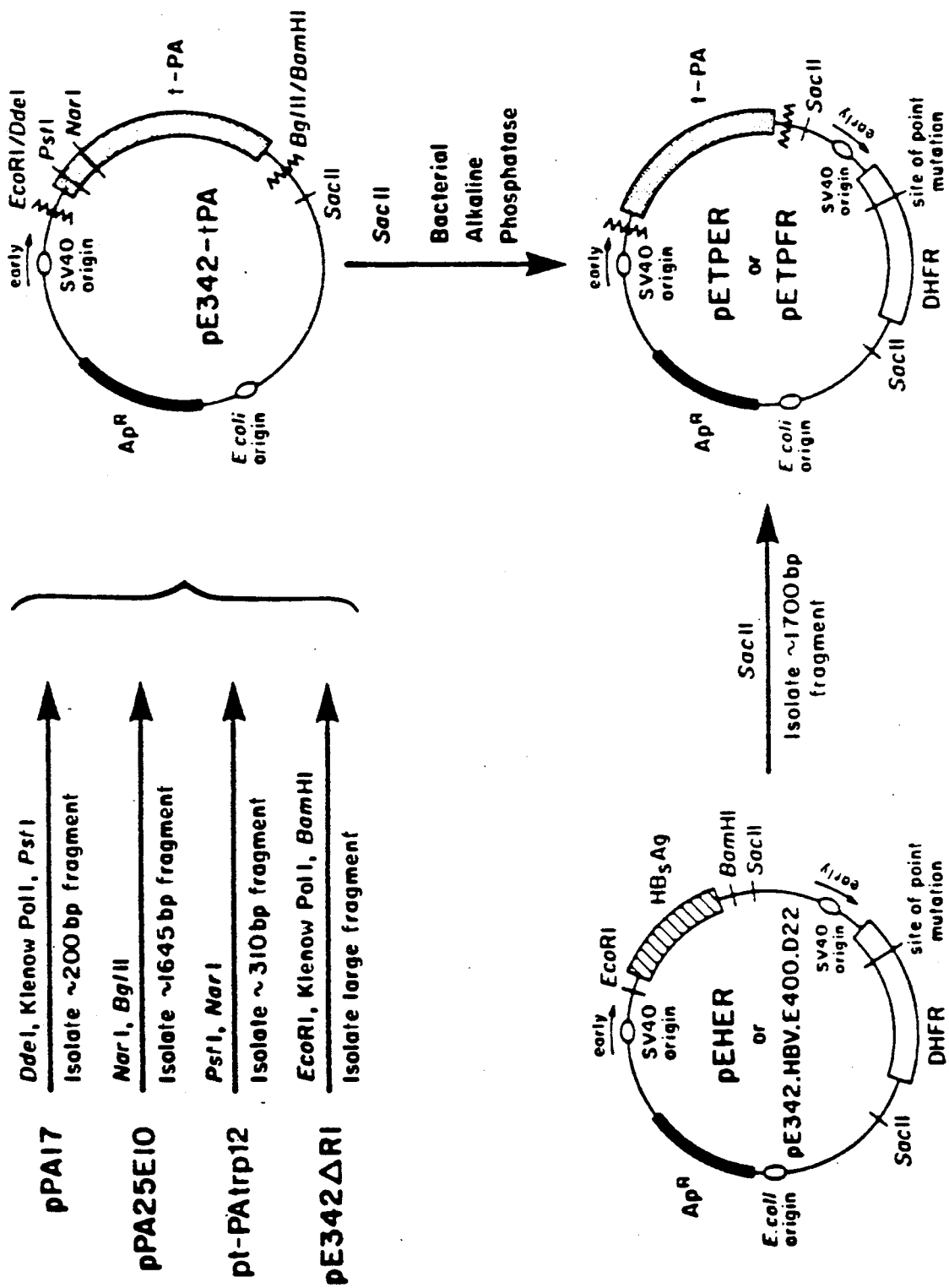
FIG. 1 is a schematic representation of how plasmid pETPFR (pPADHFR-6) can be prepared and demonstrates also a partial restriction mapping thereof.

The following description details methods that can be employed to more specifically practice the present invention and includes details contemplated at the time as the best mode available. However detailed the following may appear in text, it should not be construed as limiting to the overall scope hereof; rather, the ambit of the present invention is governed only by the lawful construction of the appended claims.

A. Definitions/General Methods

1. Site-Specific Mutagenesis

T-PA variants in accordance herewith are preferably obtained by site-specific mutagenesis of DNA which encodes an earlier prepared variant or a nonvariant version of the protein. Site-specific mutagenesis allows the production of t-PA variants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 20 to 25 nucleotides in length is preferred, with about 5 to 10 residues on both sides of the junction of the sequence being altered. In general, the technique of site-specific mutagenesis is well known in the art as exemplified by publications such as Adelman et al., *DNA* 2, 183 (1983), incorporated herein by reference. As will be appreciated, the technique typically employs a phage vector which exists in both a single stranded and double stranded form. Typical vectors useful in site-direct mutagenesis include vectors such as the M13 phage, for example, as disclosed by Messing et al., *Third Cleveland Symposium on Macromolecules and Recombi-*

*nant DNA*, Editor A. Walton, Elsevier, Amsterdam (1981) incorporated herein by reference. These phages are readily commercially available and their use is generally well known to those skilled in the art. Alternatively, plasmid vectors that contain a single-stranded phage origin of replication (Veira et al., *Meth. Enzymol.* 153, 3 (1987)) may be employed in order to obtain single-stranded DNA.

In general, site-directed mutagenesis in accordance herewith is performed by first obtaining a single-stranded vector which includes within its sequence a DNA sequence which encodes tissue plasminogen activator. An oligonucleotide primer bearing the desired mutated sequence is prepared, generally synthetically, for example by the method of Crea et al., *Proc. Natl. Acad. Sci. U.S.A.* 75, 5765 (1978). This primer is then annealed with the single-stranded t-PA sequence-containing vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells such as JM101 cells and clones are selected which include recombinant vectors bearing the mutated sequence arrangement.

After such a clone is selected, the mutated t-PA region may be removed and placed in a appropriate vector for t-PA production, generally an expression vector of the type which may be employed for transformation of an appropriate eukaryotic host. In the context of the present invention, CHO cells or 293 cells are preferred for the preparation of long-term stable t-PA producers. However, the invention is not limited to CHO production as it is known that numerous other cell types may be employed, particularly where one desires only transient production of the enzyme for test purposes. For example, described below is a transient system employing 293 cells (Graham et al., *J. Gen. Virol.* 36, 59 (1977)) which provide a convenient system for production of t-PA variants for analytical purposes.

2. Host Cell Cultures and Vectors

Although CHO expression is ultimately preferred for t-PA production, the vectors and methods disclosed herein are suitable for use in host cells over a wide range of prokaryotic and eukaryotic organisms.

In general, of course, prokaryotes are preferred for the initial cloning of DNA sequences and constructing the vectors useful in the invention. For example, *E. coli* K12 strain 294 (ATCC No. 31446) is particularly useful. Other microbial strains which may be used include *E. coli* strains such as *E. coli* B, and *E. coli* X1776 (ATTC No. 31537). These examples are, of course, intended to be illustrative rather than limiting.

Prokaryotes may also be used for expression. The aforementioned strains, as well as *E. coli* W3110 (F-, lambda-, prototrophic, ATTC No. 273325), bacilli such as *Bacillus subtilus*, and other enterobacteriaceae such as *Salmonella typhimurium* or *Serratia marcesans*, and various pseudomonas species may be used.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR 322, a plasmid derived from an *E. coli* species (see, e.g., Bolivar et al., *Gene* 2, 95 (1977)). pBR 322 contains genes for ampicillin and tetracycline resistance and thus provides easy means for identifying transformed cells. The pBR 322 plasmid, or other microbial plasmid or phage must also contain, or be modified to contain, promoters which can be used by the microbial organism for expression of its own proteins.

Those promoters most commonly used in recombinant DNA construction include the *B. lactase* (penicillinase) and lactose promoter systems (Chang et al., *Nature* 375, 615 (1978); Itakura et al., *Science* 198, 1056 (1977); Goeddel et al., *Nature* 281, 544 (1979)) and a tryptophan (trp) promoter system Goeddel et al., *Nucleic Acids Res.* 8, 4057 (1980); EPO Appl. Publ. No. 0036776). While these are the most commonly used, other microbial promoters have been discovered and utilized, and details concerning their nucleotide sequences have been published, enabling a skilled worker to ligate them functionally with plasmid vectors (see, e.g. Siebenlist et al., *Cell* 20, 269 (1980)).

In addition to prokaryotes, eukaryotic microbes, such as yeast cultures may also by used. *Saccharomvces cerevisiae*, or common baker's yeast is the most commonly used among eukaryotic microorganisms, although a number of other strains are commonly available. For expression in *Saccharomyces*, the plasmid YRp7, for example, (Stinchcomb et al., *Nature* 282 39 (1979); Kingsman et al., *Gene* 7, 141 (1979); Tschemper et al., *Gene* 10, 157 (1980)) is commonly used. This plasmid already contains the trol gene which provides a selection marker for a mutant strain of yeast lacking the ability to grow in tryptophan, for example ATCC No. 44076 or PEP4-1 (Jones, *Genetics* 85, 12 (1977)). The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase (Hitzeman et al., *J. Biol. Chem.* 255, 2073 (1980)) or other glycolytic enzymes (Hess et al., *J. Adv. Enzyme Reg.* 7: 149 (1968); Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing yeast-compatible promoter, origin of replication and termination sequences is suitable.

In addition to microorganisms, cultures of cells derived from multicellular organisms may also be used as hosts. In principle, any such cell culture is workable, whether from vertebrate or invertebrate culture. However, interest has been greatest in vertebrate cells, and propagation of vertebrate cells in culture (tissue culture) has become a routine procedure in recent years [*Tissue Culture*, Academic Press, Kruse and Patterson, editors (1973)]. Examples of such useful host cell lines are VERO and HeLa cells, Chinese hamster ovary (CHO) cell lines, and W138, BHK, COS-7, 293 and MDCK cell lines. Expression vectors for such cells ordinarily include (if necessary) an origin of replication, a promoter located in front of the gene to be expressed, along with any necessary ribosome binding sites, RNA splice sites, polyadenylation sites, and transcriptional terminator sequences.

For use in mammalian cells, the control functions on the expression vectors are often provided by viral material. For example, commonly used promoters are derived from polyoma, Adenovirus2, and most frequently Simian Virus 40 (SV40). The early and late promoters of SV40 virus are particularly useful because both are obtained easily from the virus as a fragment which also contains the SV40 viral origin of replication (Fiers et al., *Nature* 273, 113 (1978). Smaller or larger SV40 fragments may also be used, provided there is included the approximately 250 bp sequence extending from the HindIII site toward the BglI site located in the viral origin of replication. Further, it is also possible, and often desirable, to utilize promoter or control sequences normally associated with the desired gene sequence, provided such control sequences are compatible with the host cell systems.

An origin of replication may be provided either by construction of the vector to include an exogenous origin, such as may be derived from SV40 or other viral (e.g Polyoma, Adeno, VSV, BPV) source, or may be provided by the host cell chromosomal replication mechanism. If the vector is integrated into the host cell chromosome, the latter is often sufficient.

In selecting a preferred host cell for transfection by the vectors of the invention which comprise DNA sequences encoding both variant t-PA and DHFR protein, it is appropriate to select the host according to the type of DHFR protein employed. If wild type DHFR protein is employed, it is preferable to select a host cell which is deficient in DHFR, thus permitting the use of the DHFR coding sequence as a marker for successful transfection in selective medium which lacks hypoxanthine, glycine, and thymidine. An appropriate host cell in this case is the Chinese hamster ovary (CHO) cell line deficient in DHFR activity, prepared and propagated as described by Urlaub and Chasin, *Proc. Natl. Acad. Sci.* (USA) 77, 4216 (1980).

On the other hand, if DHFR protein with low binding affinity for MTX is used as the controlling sequence, it is not necessary to use DHFR deficient cells. Because the mutant DHFR is resistant to methotrexate, MTX containing media can be used as a means of selection provided that the host cells are themselves methotrexate sensitive. Most eukaryotic cells which are capable of absorbing MTX appear to be methotrexate sensitive. One such useful cell line is a CHO line, CHO.K1 (ATCC No. CCL 61).

Satisfactory amounts of human t-PA are produced by cell cultures, however refinements, using a secondary coding sequence serve to enhance production levels even further. The secondary coding sequence comprises dihydrofolate reductase (DHFR) which is affected by an externally controlled parameter, such as methotrexate, thus permitting control of expression by control of the methotrexate (MTX) concentration.

3. Typical Methodology Employable

If cells without formidable cell membrane barriers are used as host cells, transfection is carried out by the calcium phosphate precipitation method as described by Graham and Van der Eb, *Virology* 52, 546 (1978). However, other methods for introducing DNA into cells such as by nuclear injection or by protoplast fusion may also be used.

If prokaryotic cells or cells which contain substantial cell wall constructions are used, the preferred method of Cohen et al., *Proc. Natl. Acad. Sci.* (USA) 69, 2110 (1972).

Construction of suitable vectors containing the desired coding and control sequences employ standard ligation techniques.

Isolated plasmids or DNA fragments are cleaved, tailored, and relegated in the form desired to form the plasmids required.

Cleavage is performed by treating with restriction enzyme or enzymes) in suitable buffer. In general, about 1 $\mu$g plasmid or DNA fragments is used with about 1 unit of enzyme in about 20 $\mu$l of buffer solution. (Appropriate buffers and substrate amounts for particular restriction enzymes are specified by the manufacturer.) Incubation times of about 1 hour at 37° C. are workable. After incubation, protein is removed by extraction with phenol and chloroform, and the nucleic acid is recovered from the aqueous fraction by precipitation with ethanol.

If blunt ends are required, the preparation may be treated for 15 minutes at 15° C. with 10 units of Polymerase I (Klenow), phenol-chloroform extracted, and ethanol precipitated.

Size separation of the cleaved fragments is performed using percent polyacrylamide gel described by Goeddel et al., *Nucleic Acids Res.* 8, 4057 (1980).

For ligation approximately equimolar amounts of the desired components, suitably end tailored to provide correct matching are treated with about 10 units T4 DNA ligase per 0.5 $\mu$g DNA. (When cleaved vectors are used as components, it may be useful to prevent religation of the cleaved vector by pretreatment with bacterial alkaline phosphatase.)

As discussed above, t-PA variants are preferably produced by means of specific mutation Mutants useful in the practice of the present invention are formed most readily through the use of specific oligonucleotide sequences which encode the DNA sequence of the desired deletion junctions, as well as a sufficient number of adjacent nucleotides, to provide a sequence of sufficient size and sequence complexity to form a stable duplex on both sides of the deletion junction being traversed.

For analysis to confirm correct sequences in plasmids constructed, the ligation mixtures are typically used to transform *E. coli* K 12 strain 294 (ATCC 31446) or other suitable *E. coli* strains, and successful transformants selected by ampicillin or tetracycline resistance where appropriate. Plasmids from the transformants are prepared, analyzed by restriction mapping and/or DNA sequencing by the method of Messing et al., *Nucleic Acids Res.* 9, 309 (1981) or by the method of Maxam et al., *Methods of Enzymology* 65, 499 (1980).

After introduction of the DNA into the mammalian cell host and selection in medium for stable transfectants, amplification of DHFR protein coding sequences is effected by growing host cell cultures in the presence of approximately 20–500,000 nM concentrations of methotrexate, a competitive inhibitor of DHFR activity. The effective range of concentration is highly dependent, of course, upon the nature of the DHFR gene, protein and the characteristics of the host. Clearly, generally defined upper and lower limits cannot be ascertained. Suitable concentrations of other folic acid analogs or other compounds which inhibit DHFR could also be used. MTX itself is, however, convenient, readily available and effective.

B. Preparation of Comparative Variants of t-PA

The construction of plasmid pCVSVPA-N44 D22 is described in detail infra in connection with the description of the preparation of plasmid p1154.

Likewise, site directed mutagenesis experiments are discussed in detail infra in connection with the preparation of plasmid pPADHFR-6 2C9.

Figure 3:
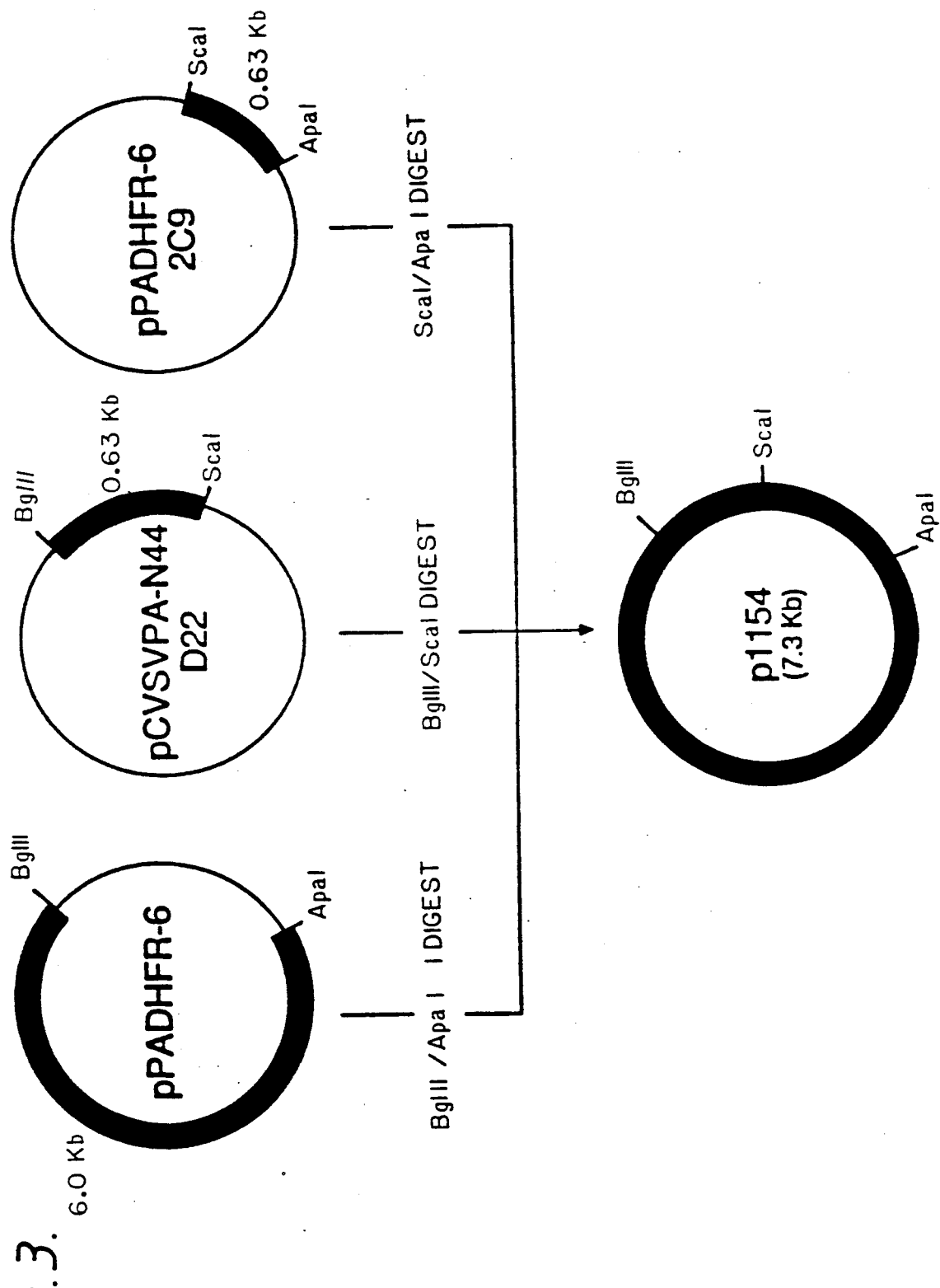
FIG. 3 is a schematic representation of how plasmid p1154 can be prepared and demonstrates also a partial restriction mapping thereof.

The des 44–84 growth factor domain deletion, des 92–179 Kringle 1 domain deletion, and des 174.261 Kringle 2 domain deletion were also made by site-directed mutagenesis using the following oligonucleotides:

```
des 44-84    GCAGGGCACAGTGCGAAATAGATACTCGAGCCACGTGCTACG des 92-179   TGTGAAATAGATACTCGAGCCACGTGCTACTTTGGGAATGGATCCGCCTACCGTGGC des 174-261  TTCTGCAGCACCCCTGCCTGCTCCACCTGCGGCCTG
```
(The delta marks indicate the site of the deleted sequence.)

and these used to prepare expression plasmids in a manner analogous to the des 1–44 construction infra., except that mutagenesis was performed on the 1.4 kb BglII/ApaI fragment (in a single stranded vector) containing the bulk of the t-PA coding sequences—See FIG. 3. Also in a manner analogous to the des 1–44 construction, the des 44–84 and des 92–179 mutations could, in principle, also be isolated on BglII/ScaI fragments and joined to the Glu275 mutations and the t-PA C-terminal coding sequences on the 0.63 kb ScaI/ApaI fragment, thus creating plasmids similar to p1154 as described infra.

C. Preparation and Utilization of Expression Vectors for Recombinant Production of the t-PA Variants Hereof

1. Plasmid Constructions a. Plasmid p1154

1) Plasmid pPADHFR-6

Plasmid pPADHFR-6 (otherwise referred to as pETPFR) was prepared as described, for example, in European Patent Application Publication No. 93619, supra, which is hereby incorporated by reference. See FIG. 1 for perspective details. Superfluously, this plasmid, per se and in transfected form in CHO cells, has been deposited on Dec. 15, 1987 with the American Type Culture Collection, Rockville, Md., USA under ATCC Nos. 40403 and GRL 9606, respectively.

2) Plasmid pCVSVPA-N44 D22

Plasmid pCVSVPA-N44 D22 was prepared as described, for example, in U.S. Ser. No. 07/068,448, filed June 30, 1987. To recapitulate, plasmid pPADHFR-6 (supra) was digested with StuI and EcoRI to release an 826 base pair fragment which included sequences encoding the t-PA presequence through amino acid 203. This fragment was ligated with the vector fragment of SmaI/EcoRI digested M13mp1ORF, the replicative form M13 phage vector (see, e.g., Messing et al., Third Cleveland Symposium on Macromolecules Recombinant DNA, Editor A. Walton, Elsevier, Amsterdam (1981)). The intermediate plasmid, pPA-N44intA, was thus a replicative form of M13 phage which included the portion of the t-PA gene from which the codons for amino acids 1–44 were to be removed by site-directed deletion mutagenesis.

To perform the mutagenesis, an oligonucleotide primer was prepared by a method such as the phosphotriester method of Crea et al., Proc. Natl. Acad. Sci. (USA) 75, 5765 (1978). The primer employed to prepare a des (1–44) mutant was as follows:

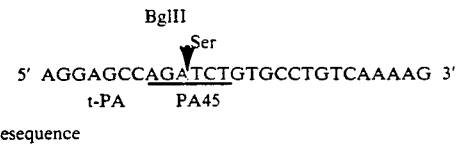

As will be appreciated, the ten 5' nucleotides of this primer encode presequence amino acids =3 to -1 (gly-ala-arg), whereas the seventeen 3' nucleotides encode amino acids 45 through 49 (SER-VAL-PRO-VAL-LYS). Note that the "TCT" codon was employed for serine-45 in order to retain the BglII site.

Approximately 200 mg of the synthetic oligonucleotide was phosphorylated for 30 minutes at 37° C. in 30 μl of 50 mM-Tris-HCl, pH 7.5, 10 mM MgCl$_2$, 10 mM dithiothreitol, 1 mM ATP containing about 8 U of T4 polynucleotide kinase. For heteroduplex formation, about 50 ng single-stranded pPA-N44intA was heated to 95° C. (10 min), and slowly cooled to room temperature (30 min), then to 4° C., in about 40 μl 10 mM Tris-HCl, pH 7.5, 10 mM MgCl$_2$, 1 mM dithiothreitol containing 100 ng of the phosphorylated primer. Primer extension was started by the addition of 10 μl ligase buffer containing 2 mM ATP, 0.25 mM each of dGTP, dCTP, dATP, dTTP, 5 U of E. coli polymerase I large (Klenow) fragment and 400 U of T4 DNA ligase. After 1 hour at 15° C. the reaction mixture was used to transform JM101 cells.

Transformation was performed by mixing all of the ligation mixture with 200 μl of competent JM101 cells, followed by incubation on ice for 30' and 5' at 37° C. Then 3.5 ml 2YT top agar at 55° C. was mixed with 200 μl of the phage-saturated cells, 10 μl IPTG (200 mM) and 50 μl X gal and after addition, the cells were plated onto Petri dishes containing 2YT with no drugs.

Colorless plaques were picked and transferred to a microtiter dish containing 100 μl 2YT medium. The inoculated microtiter fluids were stamped on 15 cm diameter LB agar plates overlayed with a lawn of 600 μl JM101 cells in 8 ml 2YT top agar and incubated overnight at 37° C. The formed plaques were transferred to a nitrocellulose disc by physical contact for 1 min. The nitrocellulose disc was treated with 0.5 M NaOH, 1.5 M NaCl for 3 min and washed twice with 3 M NaCl.0.5 M Tris-HCl pH 7.5 for 15 min and then with 2X SSC for 15 min. Prehybridization mix contains 10 mM Tris pH 7.5, 5 mM EDTA, 0.9 M NaCl, 1X Denhardt 0.5 percent NP40, 100 μM ATP, 1 mM sodium pyrophosphate, 1 mM sodium phosphate and 50 µg/ml *E. coli* tRNA. 1X Denhardt's contains per liter 200 mg Ficoll, 200 mg polyvinylpyrrolidone, 200 mg bovine serum albumin (BSA; fraction V). The disc was baked at 80° C. in vacuo for 90 min. The disc was then incubated for 3 hrs with 6 ml prehybridization fluid in a Petri dish followed by addition of 5×10$^6$ cpm labeled primer and hybridized overnight. Selective washing of the disc was performed with 0.4X SSC at 49° C. and after air-drying the disc was exposed to X-ray film. Positively hybridizing clones were further analyzed by dideoxy sequencing. See Aldeman, supra. From the positive colonies, a recombinant plasmid, designated pPA-N44intA delta, was selected which contained the proper deletion.

In order to replace the mutant gene sequence from the M13 phage into proper expression context into the DHFR-containing expression vector, plasmid pPADHFR.6 was digested separately with BglI/KpnI, to isolate the large fragment encoding the DHFR gene, and BstXI/KpnI, to isolate a 2240 base fragment encoding the 3' end (amino acids 45-527) of natural t-PA. A 400 base fragment bearing the N44 (des 1-44) mutation was isolated from pPA.N44intA delta by digestion with BglII/BstXI, and ligated together with the two fragments derived from pPADHFR-6. The product of this ligation, designated CVSVPA-N44 D22, was thus a copy of the parental plasmid pPADHFR-6, except having codons encoding amino acids 1-44 removed.

Figure 2:
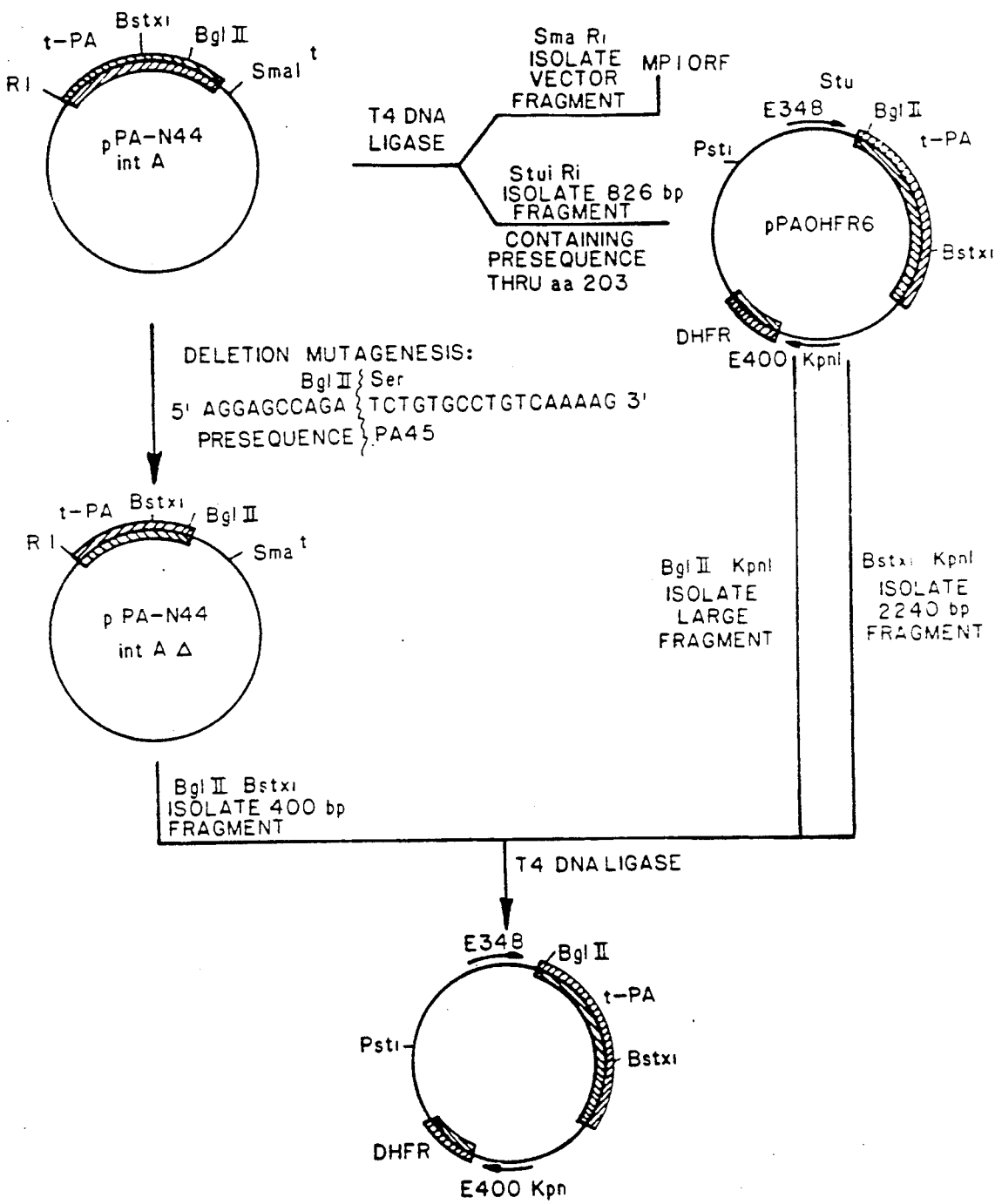
FIG. 2 is a schematic representation of how plasmid pCVSVPA-N44D22 can be prepared and demonstrates also a partial restriction mapping thereof.

See FIG. 2 for perspective details.

3) Plasmid pPADHFR-6 2C9

Plasmid pPADHFR-6 2C9 was prepared as described, for example, in U.S. Ser. No. 07/071,506, filed July 9, 1987 and its parents see supra. In summary, human t-PA DNA was obtained from plasmids pPADHFR-6 (also designated pETPFR) and pA25EIO. The preparation of these two t-PA plasmids is described in European Patent Application Publication No. 093619, supra.

Plasmid pA25EIO contains sequences coding for the last 508 amino acids of the t-PA gene and 772 base pairs of the 3' untranslated region. This plasmid was digested with SacI and BglII to produce a 744 base pair fragment which was isolated by standard methods as previously described. This fragment contains the codons for t-PA amino acids 411 through 527 and includes part of the 3' untranslated region.

Plasmid pPADHFR-6 contains the entire structural gene for t-PA and part of the 3' untranslated region. This plasmid was digested with SacI and BglII to produce a 1,230 base pair fragment which was isolated. This fragment contains codons for the first amino acids of the mature form of t-PA.

These fragments were ligated together using standard methods and digested with BglII. A 1,974 base pair fragment containing codons for the entire mature t-PA sequence plus part of the 3' untranslated region was isolated. Double stranded M13mp8, (Messing, supra.) was digested with BamHI and annealed to the BglII digested t-PA to form M13mp8PABglII. *E. coli* JM 101 cells (ATCC No. 33876) were transformed with the double stranded replicative form of M13mp8PABglII. The single stranded and double stranded (RF) forms of M13mp8PABglII may be isolated from *E. coli* JM 101 cells infected with this phage. The single stranded form was used for the site specific mutagenesis of t-PA.

The human t-PA structural gene was modified by site specific mutagenesis to express t-PA with amino acid substitution at the appropriate various position. A synthetic oligonucleotide was prepared such as by the solid phase phosphotriester method of Crea et al. (supra.). Among the synthetic primers that were prepared and used for such site specific mutagenesis was:

```
Primer 2C9                        Glu
DNA Sequence   G CCT CAG TTT GAA ATC AAA GGA G
```

The procedure described hereinafter, was used to generate different t-PA clones containing the mutated sequence of the synthetic primers. The general method used is that of Adelman supra.), incorporated herein by reference. For example, 3M13RF2C9 was generated by the use of the above primer. Purified M13 RF DNA from the mutated t-PA gene was prepared from *E. coli* JM101 cells. Subsequently, DNA fragments containing the mutated t-PA DNA sequence were used to construct expression vectors for the mutated t-PA.

50 ng of a synthetic oligonucleotide was phosphorylated for 30 min at 37 C in 10 µl of 50 mM Tris-HCl pH 7.5, 10 mM MgCl$_2$, 10 mM dithiothreitol, 1 mM ATP containing 8 U of T4 polynucleotide kinase. For use as a probe, 400 ng of the synthetic oligonucleotide was phosphorylated as above except that ATP was replaced with 60 mCi [γ$^{32}$-P]-ATP (3000 µCi/mmol) resulting in approximately 50 to 60×10$^6$ cpm/400 ng of 24.mer. For heteroduplex formation, 10 ng single stranded M13mp8PABglII was heated to 95° C. (10 min), and slowly cooled to room temperature (30 min) in 40 µl 10 mM Tris-HCl pH 7.5, 10 mM MgCl$_2$, 1 mM dithiothreitol containing 10 ng of the phosphorylated primer and 50 ng of EcoRI-digested M13mp8PABglIIRF large fragment. Primer extension was started by the addition of 10 µl ligase buffer containing 2 mM ATP, 0.25 mM each of dGTP, dTTP, dCTP and dATP, 5 U of *E. coli* DNA polymerase I large fragment and 400 U of T4 DNA ligase. After 1 hr at 12° C. the reaction mixture was used to transform *E. coli* JM101 cells.

Transformation was accomplished by mixing 10 µl of the ligation mixture with 200 µl of competent JM101 cells, followed by incubation for 30 min on ice and 5 min at 37° C. Then 3.5 ml 2YT top agar at 55° C. was mixed with 200 µl saturated JM101 cells, 10 µl IPTG (200 mM) and 50 µl X gal and after addition of the transformed cells plated 9 cm on Petri dishes containing LB with no drugs.

Colorless plaques were picked and transferred to a microtiter dish containing 100 µl 2YT medium. The inoculated microtiter fluids were stamped on 15 cm diameter LB agar plates overlayed with a lawn of 600 µl JM101 cells in 8 ml 2YT top agar and incubated overnight at 37° C. The formed plaques were transferred to a nitrocellulose disc by physical contact for 1 min. The nitrocellulose disc was treated with 0.5 M NaOH, 1.5 M NaCl for 3 min and washed twice with 3 M NaCl-0.5 M Tris-HCl pH 7.5 for 15 min and then with 2X SSC for 15 min. Prehybridization mix contains 10 mM Tris pH 7.5, 5 mM EDTA, 0.9 M NaCl, 1X Denhardt 0.5 percent NP40, 100 µM ATP, 1 mM sodium pyrophosphate, 1 mM sodium phosphate and 50 µg/ml *E. coli* tRNA. 1X Denhardt's contains per liter 200 mg Ficoll, 200 mg polyvinylpyrrolidone, 200 mg bovine serum albumin (BSA; fraction V). The disc was baked at 80° C. in vacuo for 90 min. The disc was then incubated for 3 hrs with 6 ml prehybridization fluid in a Petri dish followed by addition of $5 \times 10^6$ cpm labeled primer and hybridized overnight. Selective washing of the disc was performed with 0.4X SSC at 49° C. and after air-drying the disc was exposed to X-ray film. Positively hybridizing clones were further analyzed by dideoxy sequencing. See Aldeman, (supra).

Vector fragment designated as fragment 1 was obtained by isolating the large fragment generated by digestion of pPADHFR-6 with BglII and BstEII. A fragment designated as fragment 2 was obtained by isolating the 400 base pair t-PA fragment obtained from the digestion of pPADHFR-6 with BglII and BstXI. A 1,141 base pair t-PA fragment containing the desired mutations (fragment 3) was obtained by digesting RF DNA from the mutant t-PA clones (supra.) with BstXI and BstEII. Fragments 1 and 2 were ligated with each fragment 3. The DNA mixtures were used to transform E. coli. From each of the transformants, the respective eukaryotic expression vectors were obtained, for example: pPADHFR-6 2C9.

4) Final Construction of p1154

Plasmid pETPFR was digested with the restriction enzymes BglII and ApaI and the fragments fractionated by agarose gel electrophoresis. The 6.0 kb fragment containing the t-PA preprocoding region, the SV40 early promoter, β-lactamase, and DHFR genes was cut out from the gel and electroeluted.

Plasmid pCVSVPA-N44 D22 was digested with BglII and ScaI, the fragments fractionated by acrylamide gel electrophoresis, and the band containing the 0.63 kb fragment (representing the coding sequences for the growth factor, kringle one and kringle two [partial] domains of t-PA) was cut out and electroeluted.

Plasmid pPADHFR-6 2C9 was digested with ScaI and ApaI, and the 0.63 kb fragment containing the coding sequences for kringle two (partial) and the protease (with the Glu 275 mutation) domains was purified by acrylamide gel electrophoresis and electroelution.

The three thus isolated, purified fragments were incubated in the presence of T4 DNA ligase and rATP to produce the plasmid p1154, containing sequences coding for a t-PA molecule lacking residues 1–44 (finger domain deletion) and incorporating an Arg 275→Glu mutation (single chain mutant). See FIG. 3.

b. Plasmid p652

Figure 4:
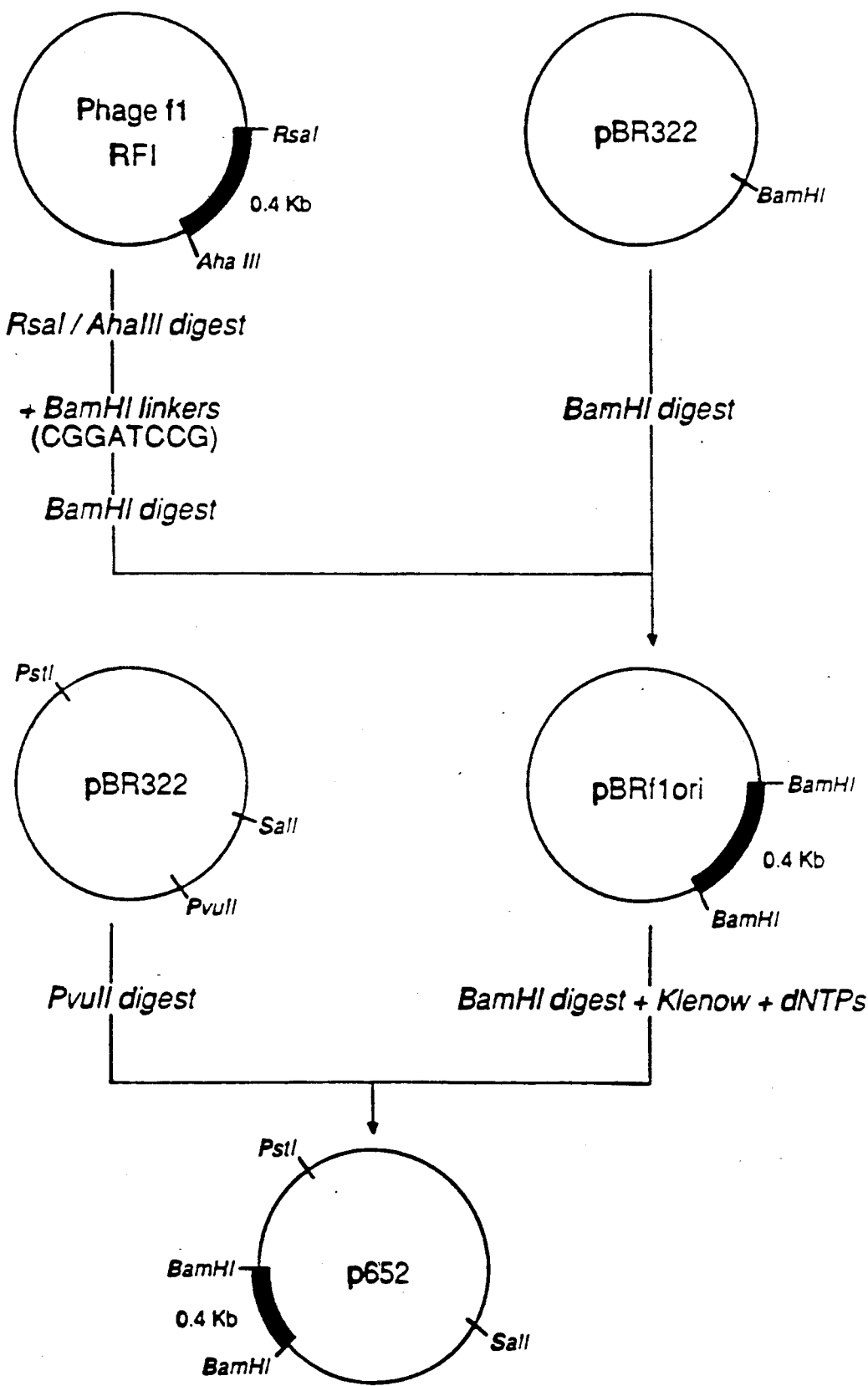
FIG. 4 is a schematic representation of how plasmid p652 can be prepared and demonstrates also a partial restriction mapping thereof.

Phage f1 RFI DNA (Zinder et al., *Microbiol. Rev.* 49, 101 (1985)) was digested with RsaI and AhaIII, and the 0.4 kb fragment containing the +strand origin of DNA replication was isolated. BamHI linkers were ligated to this fragment, then a BamHI digest was performed to produce BamHI cohesive termini. This was then inserted into the BamHI site of plasmid pBR322 (Bolivar et al., *Gene* 2, 95 (1977)) to produce plasmid, pBRflori. Plasmid pBRflori was digested with BamHI, treated with Klenow fragment of E. coli DNA polymerase I and deoxynucleoside triphosphates to create blunt ends, and the 0.4 kb fragment containing the f1+strand origin isolated. This was then inserted into the PvuII site of pBR322 to create plasmid p652. See FIG. 4.

c. Plasmid p1060

1) Plasmid pCISt-PA

Plasmid pCISt-PA was prepared as described, for example, in U.S. Ser. No. 07/071,506, filed July 9, 1987, supra. To recapitulate, the vector pCIHt-PA containing the cytomegalovirus enhancer and promoter, the cytomegalovirus splice donor site and intron, the Ig variable region splice acceptor site, the cDNA encoding t-PA (Pennica et al., *Nature* 301, 214 (1983)) and the hepatitis surface antigen polyadenylation and transcription termination site was constructed first:

The vector pF8CIS containing the cytomegalovirus enhancer (Boshart et al., *Cell* 41, 520 (1985)) and promoter (Thomsen et al., *Proc. Natl. Acad. Sci. (USA)* 81, 659 (1984)), the cytomegalovirus splice donor site and a portion of an intron (Sternberg et al., *J. of Virol.* 49, 190 (1984)), the Ig variable region intron and splice acceptor site, the cDNA encoding factor VIII and the SV40 polyadenylation site was constructed. The three parts of the construction are detailed below.

1. The ampicillin resistance marker and replication origin of the final vector was derived from the starting plasmid pUC13pML a variant of the plasmid pML (Lusky et al., *Nature* 293. 79 (1981)). pUC13pML was constructed by transferring the polylinker of pUC13 (Veira et al., *Gene* 19, 259 (1982)) to the EcoRI and HindIII sites of pML. A second starting plasmid pUC8CMV was the source of the CMV enhancer, promoter and splice donor sequence. pUC8CMV was constructed by inserting nucleotides 1 through 732 for the CMV enhancer, promoter and splice donor sequence into the blunted PstI and SphI sites of pUC8 Veira et al., supra. Synthetic BamHI.HindIII linkers (commercially available from New England Biolabs) were ligated to the cohesive BamHI end creating a HindIII site. Following this ligation a HindIII.HincII digest was performed. This digest yielded a fragment of approximately 800 bp which contained the CMV enhancer, promoter and splice donor site. Following gel isolation this 800 bp fragment was ligated to a 2900 bp piece of pUC13pML. The fragment required for the construction of pF8CIS was obtained by digestion of the above intermediate plasmid with SalI and HindIII. This 3123 bp piece contained the resistance marker for ampicillin, the origin of replication from pUC13pML and the control sequences for the CMV including the enhancer, promoter and splice donor site.

2. The Ig variable region intron and splice acceptor sequence was constructed using a synthetic oligomer. A 99-mer and a 30-mer were chemically synthesized having the following sequence for the IgG intron and splice acceptor site (Bothwell et al., *Cell* 24, 625 (1981)):

```
 1  5' AGTAGCAAGCTTGACGTGTGGCAGGCTTGA ...
31     GATCTGGCCATACACTTGAGTGACAATGA ...
60     CATCCACTTTGCCTTTCTCTCCACAGGT ...
88     GTCCACTCCCAG 3'
 1  3' CAGGTGAGGGTGCAGCTTGACGTCGTCGGA 5'
```

DNA polymerase I (Klenow fragment) filled in the synthetic piece and created a double stranded fragment (Wartell et al., *Gene* 9, 307 (1980)). This was followed by a double digest of PstI and HindIII. This synthetic linker was cloned into pUC13 (Veira et al., supra) at the PstI and HindIII sites. The clone containing the synthetic oligonucleotide, labeled pUCIg.10, was digested with PstI. A ClaI site was added to this fragment by use of a PstI. ClaI linker. Following digestion with HindIII and 118 bp piece containing part of the Ig intron and the Ig variable region splice acceptor was gel isolated.

3. The third part of the construction scheme replaced the hepatitis surface antigen 3' end with the polyadenylation site and transcription termination site of the early region of SV40. A vector, pUC.SV40 containing the SV40 sequences was inserted into pUC8 at the BamHI site described in Veira et al., supra. pUC.SV40 was then digested with EcoRI and HpaI. A 143 bp fragment containing only the SV40 polyadenylation site was gel isolated from this digest. Two additional fragments were gel isolated following digestion of pSVE.8clD (European Patent Application Publication No. 160457). The 4.8 kb fragment generated by EcoRI and ClaI digest contains the SV40-DHFR transcription unit, the origin of replication of pML and the ampicillin resistance marker. The 7.5 kb fragment produced following digestion with ClaI and HpaI contains the cDNA for factor VIII. A three-part ligation yields pSVE.8c24D. This intermediate plasmid was digested by ClaI and SalI to give a 9611 bp fragment containing the cDNA for factor VIII with and SV40 polyadenylation and transcription termination sites followed by the SV40 DHFR transcription unit.

The final three part ligation to yield pF8CIS used: a) the 3123 bp SalI-HindIII fragment containing origin of replication, the ampicillin resistance to marker and the CMV enhancer, promoter and splice donor; b) the 118 bp HindIII-ClaI fragment containing the Ig intron and splice acceptor; and, c) a 9611 bp ClaI.SalI fragment containing the cDNA for factor VIII, SV40 polyadenylation site and the SV40 DHFR transcription unit.

Figure 5A:
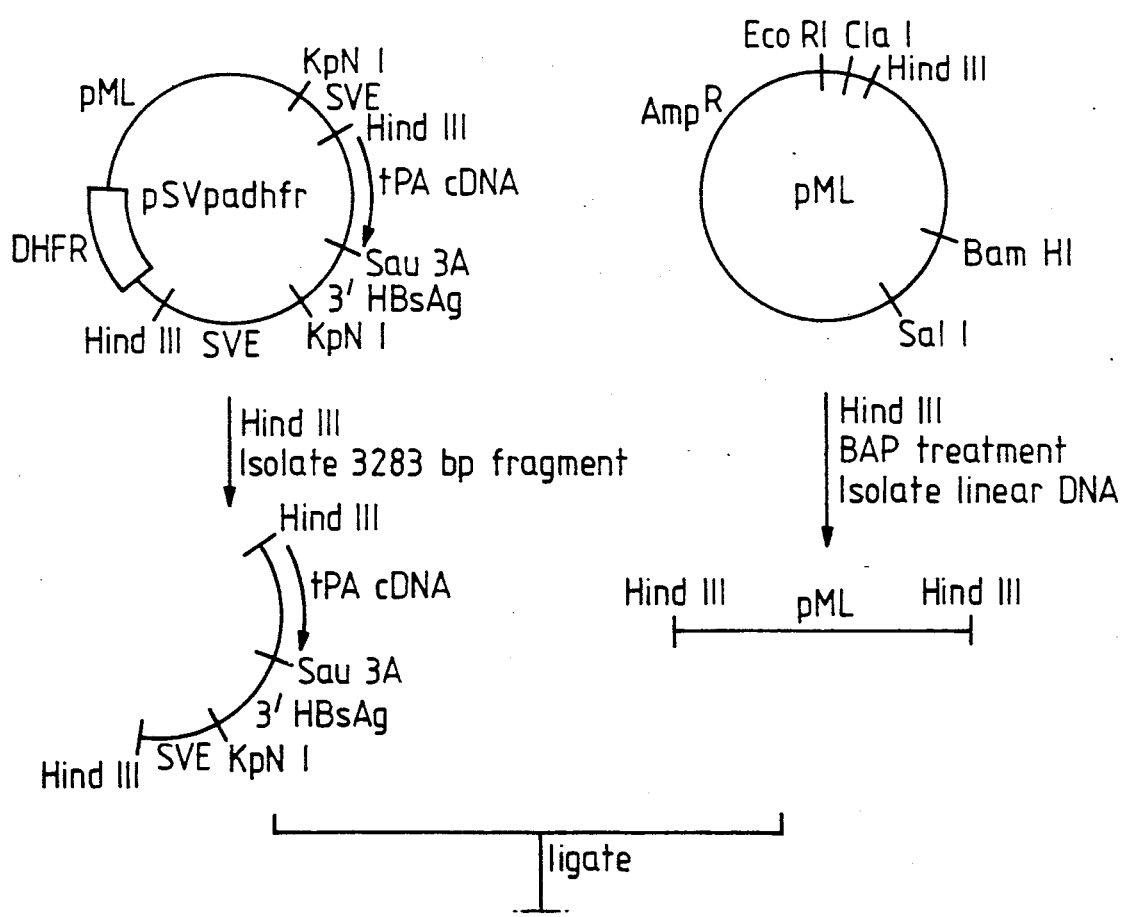
FIGS. 5, 5a, 6a, and 6b are schematic representations of how plasmid pCISt-PA can be prepared and demonstrate also a partial restriction mapping thereof.
Figure 5B:
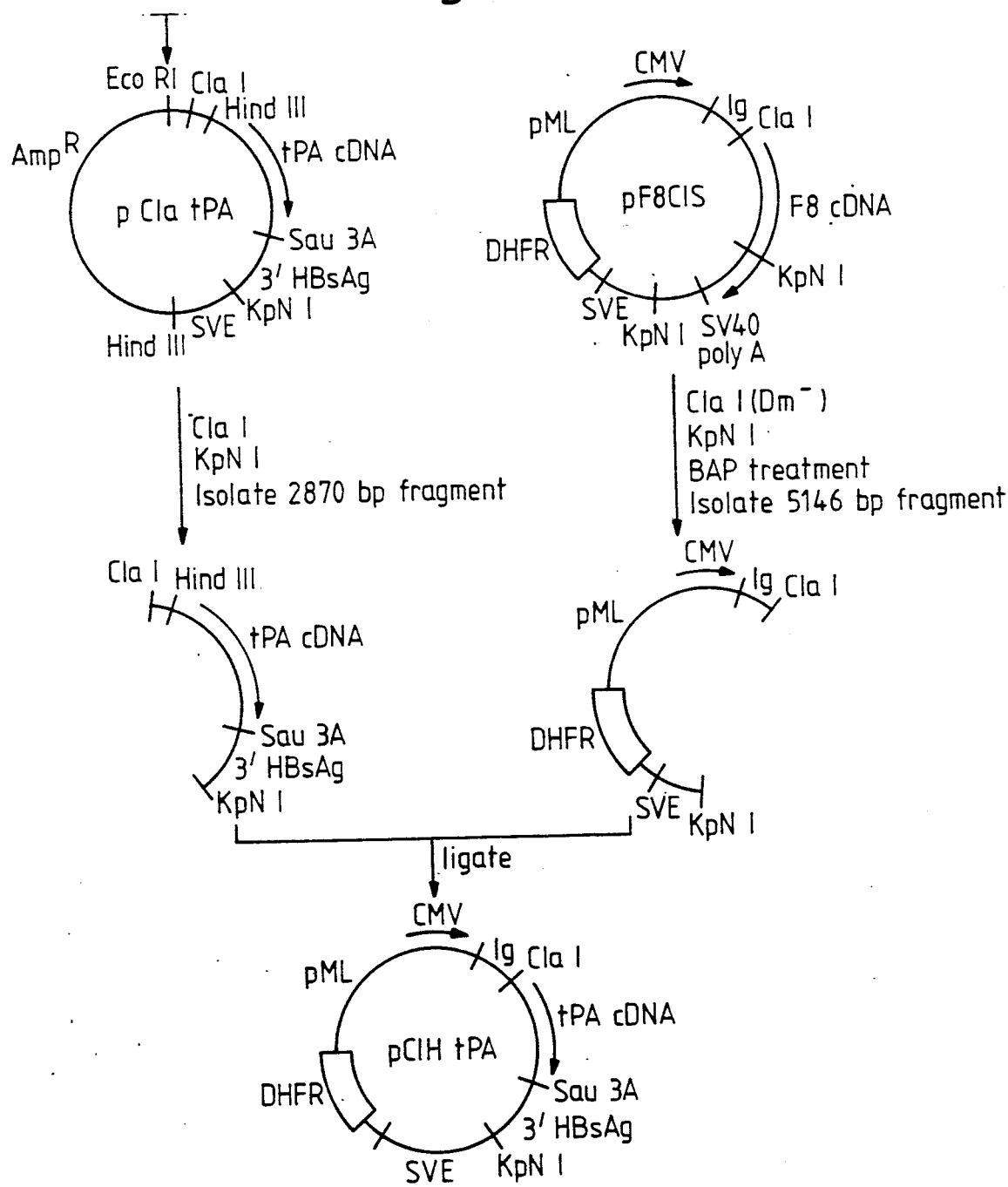

Next, the completion of the construction of plasmid pCIH t-PA from intermediate plasmid pCla t-PA and plasmid pF8CIS (above) was undertaken:

The t-PA cDNA was first cloned into pML to provide a ClaI site at the 5' end of the gene. To do this a 3238 bp HindIII fragment from pSVpa-DHFR (otherwise referred to as pETPFR supra.) was inserted into the HindIII site of pML (Lusky et al., supra.). Colonies were screened for clones which have the 5' end of the cDNA juxtaposed to the ClaI site. The intermediate plasmid was labeled co pCLAt-PA. A t-PA cDNA followed by the 3' polyadenylation regions was isolated as a ClaI.KpnI fragment of 2870 bp. This fragment was ligated to the 5146 bp fragment of pF8CIS. This ClaI.KpnI fragment of the CIS vector provided the 5' control region, a SV40-DHFR transcriptional unit, the ampicillin resistance gene and origin region from pML. See FIG. 5.

Expression levels of t-PA were obtained by transfecting CHO and 293 cells with pCIHt-PA, in accordance with methods generally known per se and described supra. Media from the transfected 293 cells, for example, were assayed demonstrating that pCIH t-PA produced 420 ng/ml of t-PA.

Figure 6A:
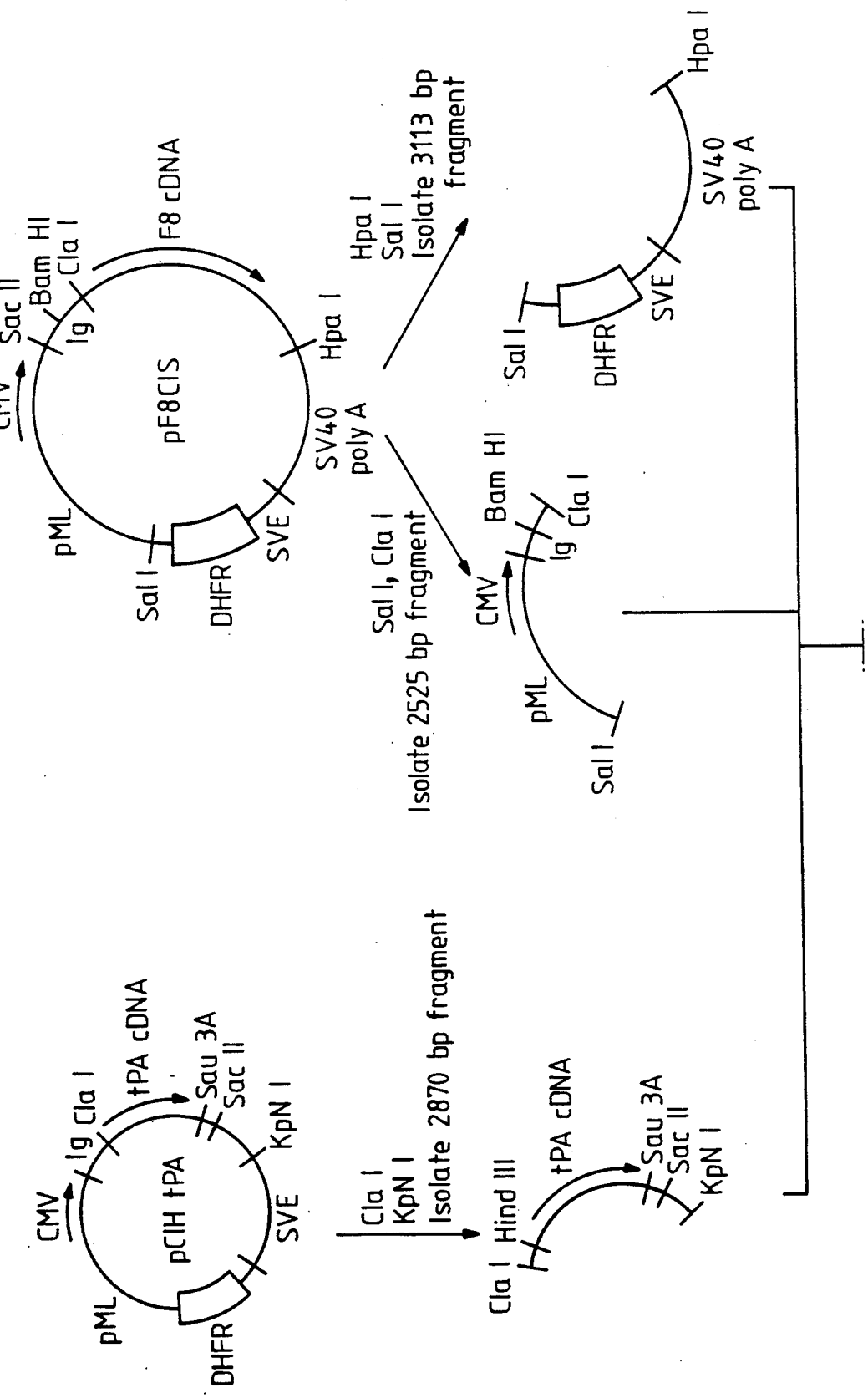
Figure 6B:
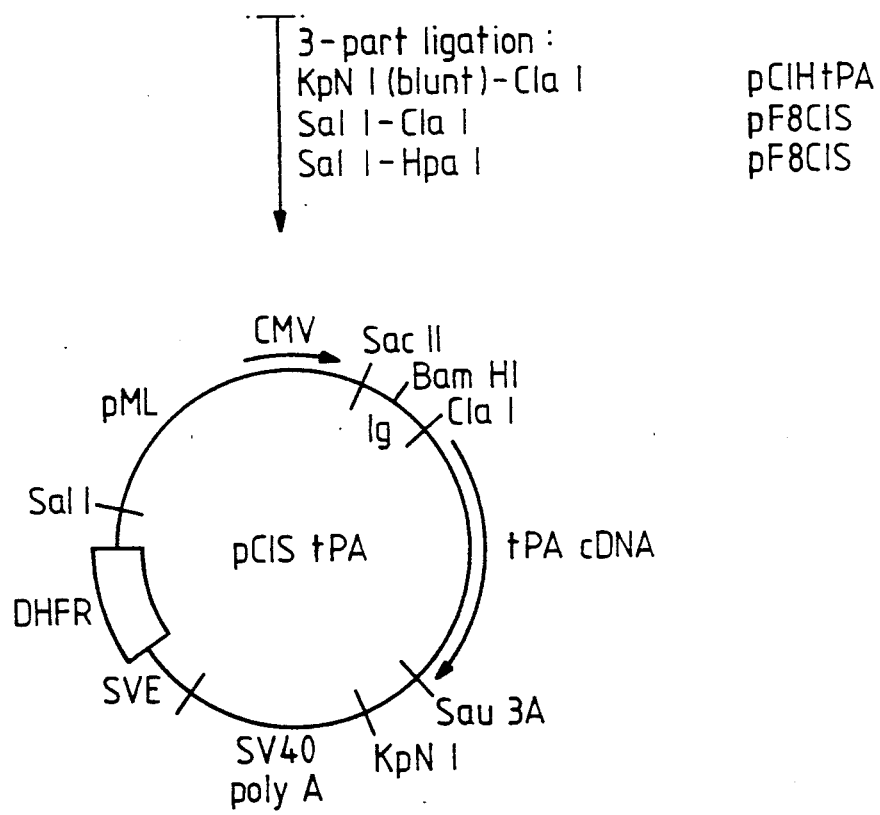

The vector pCISt-PA containing the cytomegalovirus enhancer and promoter, the cytomegalovirus splice donor site and intron, the Ig variable region splice acceptor site, the cDNA encoding t-PA and the pSV40 polyadenylation sequence was finally constructed:

The starting vectors for this construction were pCIHt-PA and pF8CIS (supra). The latter vector has the same 5' controls as pCIHt-PA but includes the cDNA for factor VIII and the SV40 polyadenylation site. SacII was used to cleave 3' of the t-PA cDNA. The resultant 3' overhang was blunted by T4 polymerase. pCIH t-PA was then cut with ClaI. This site separates the chimeric intron cleaving between the CMV intronic sequences and the Ig variable region intron. An 2870 bp fragment was gel isolated from the ClaI treatment. The SV40 polyadenylation site, DHFR, transcription control, bacterial origin of replication and amp$^r$ gene, as well as the CMV enhancer and promoter and splice donor were isolated from pF8CIS. These elements were isolated into fragments as a 2525 bp Sal.BamHI fragment and a HpaI-Sal and 3113 bp fragment. A three part ligation of the KpnI(blunt)-ClaI fragment with the HpaI-Sal fragment and Sal to BamHI fragment yields pCIS t-PA, which was expressed in both CHO and 293 cells as discussed above for plasmid pCIH t-PA giving 55 and 3000 ng/ml of t-PA respectively. See FIG. 6.

(Incorporated by reference herein is the subject matter of U.S. Ser. No. 06/907,185, filed Sept. 12, 1986 and its continuing application U.S. Ser. No. 07/071,674, filed July 9, 1987.)

2) Final Construction of p1060

Figure 7:
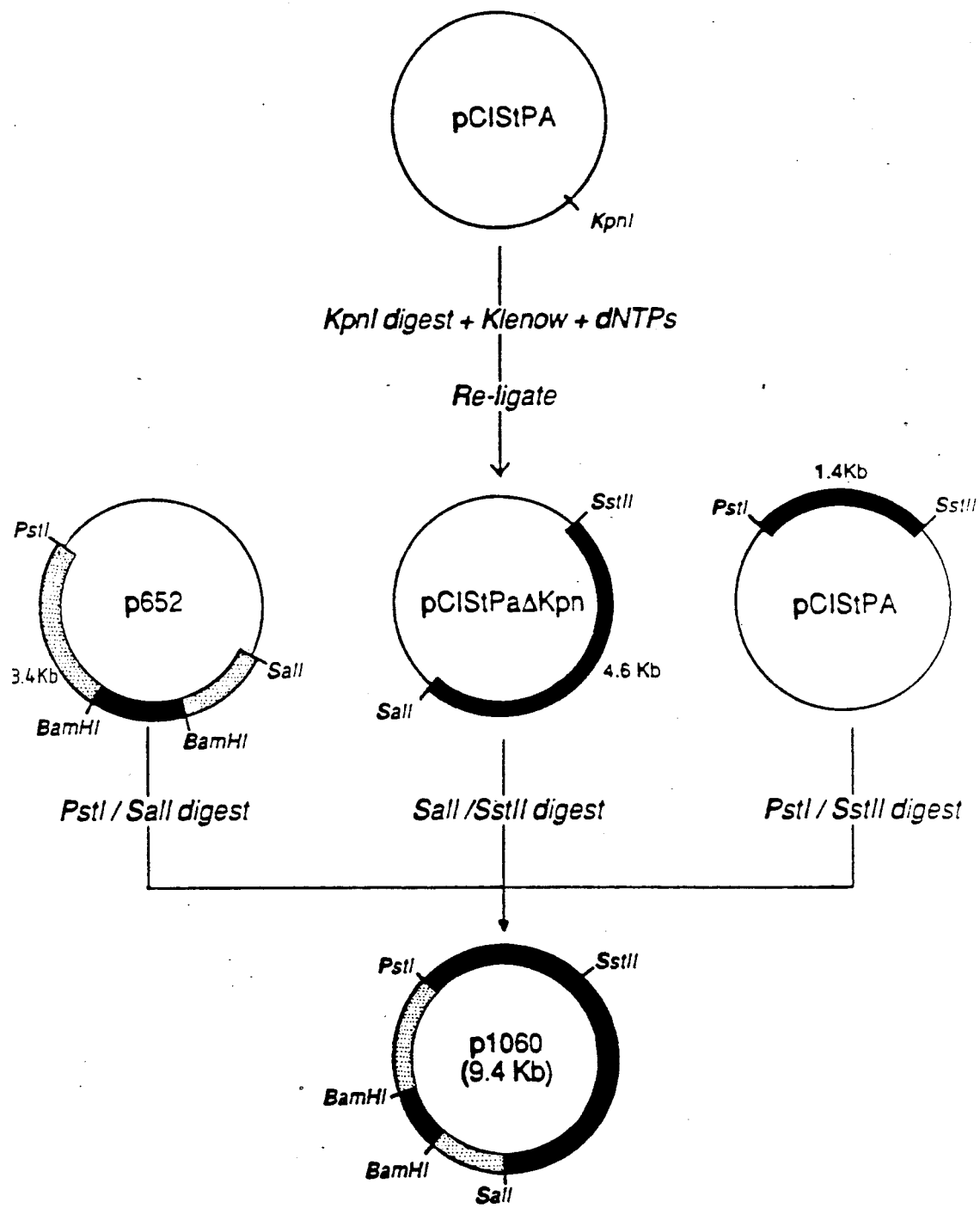
FIG. 7 is a schematic representation of how plasmid p1060 can be prepared and demonstrates also a partial restriction mapping thereof.

Plasmid pCIS t-PA was digested with KpnI, treated with E. coli DNA polymerase I Klenow fragment and deoxyribonucleoside triphosphates to create blunt ends, and recircularized via intrmolecular ligation. This treatment destroyed the KpnI site, producing a plasmid termed pCIS t-PA ΔKpn. Plasmid pCIS t-PA AKpn was digested with SalI and SstII, and the 4.6 kb fragment isolated. Additional plasmid pCISt-PA was digested with PstI and SstII and the 1.4 kb fragment isolated. Plasmid p652 was digested with PstI and SalI and the 3.4 kb fragment isolated. These three fragments were joined in a three-way ligation to produce plasmid p1060. See FIG. 7.

d. Plasmid p1179

Figure 8:
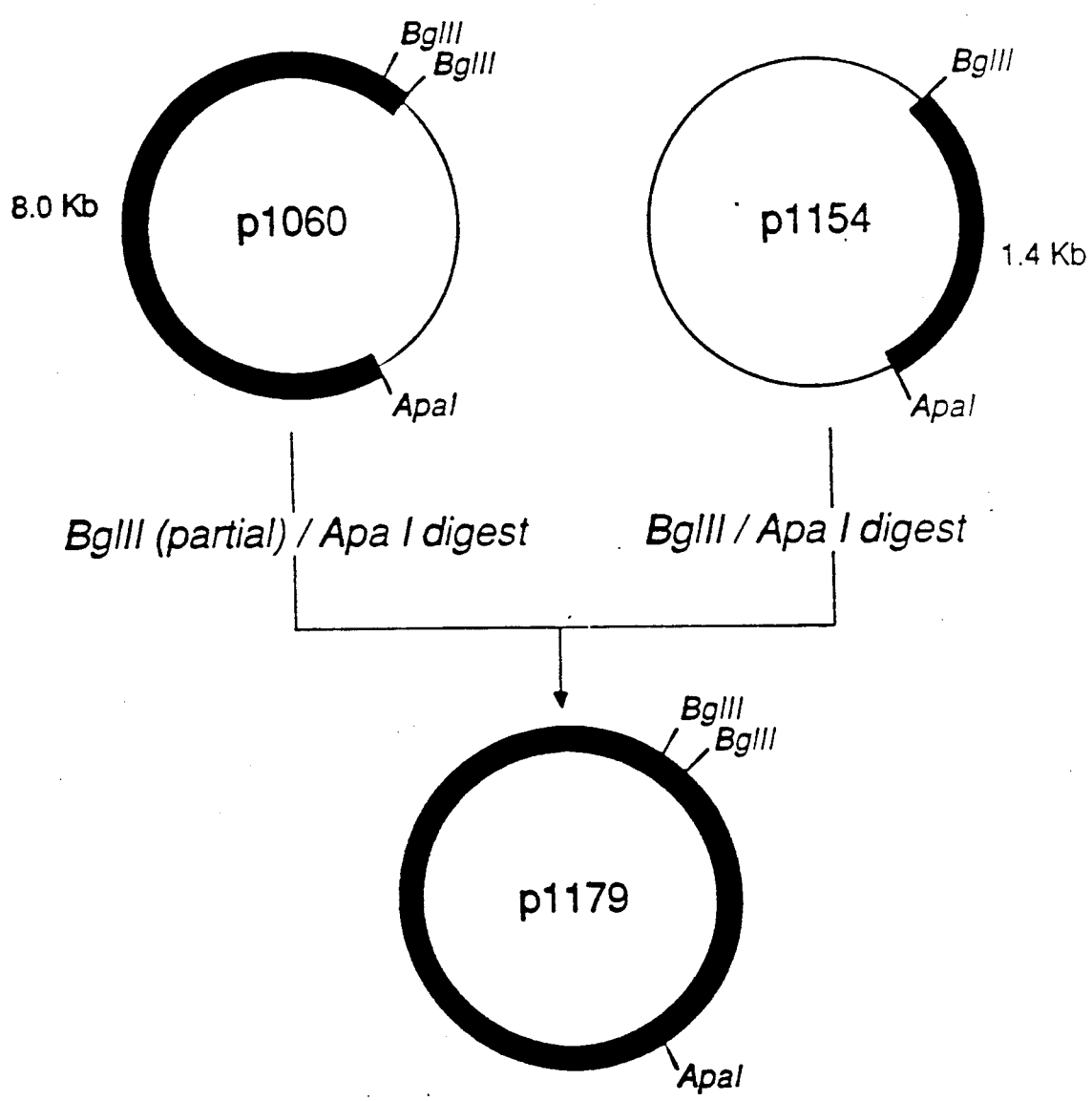
FIG. 8 is a schematic representation of how plasmid p1179 can be prepared and demonstrates also a partial restriction mapping thereof.
Figure 10:
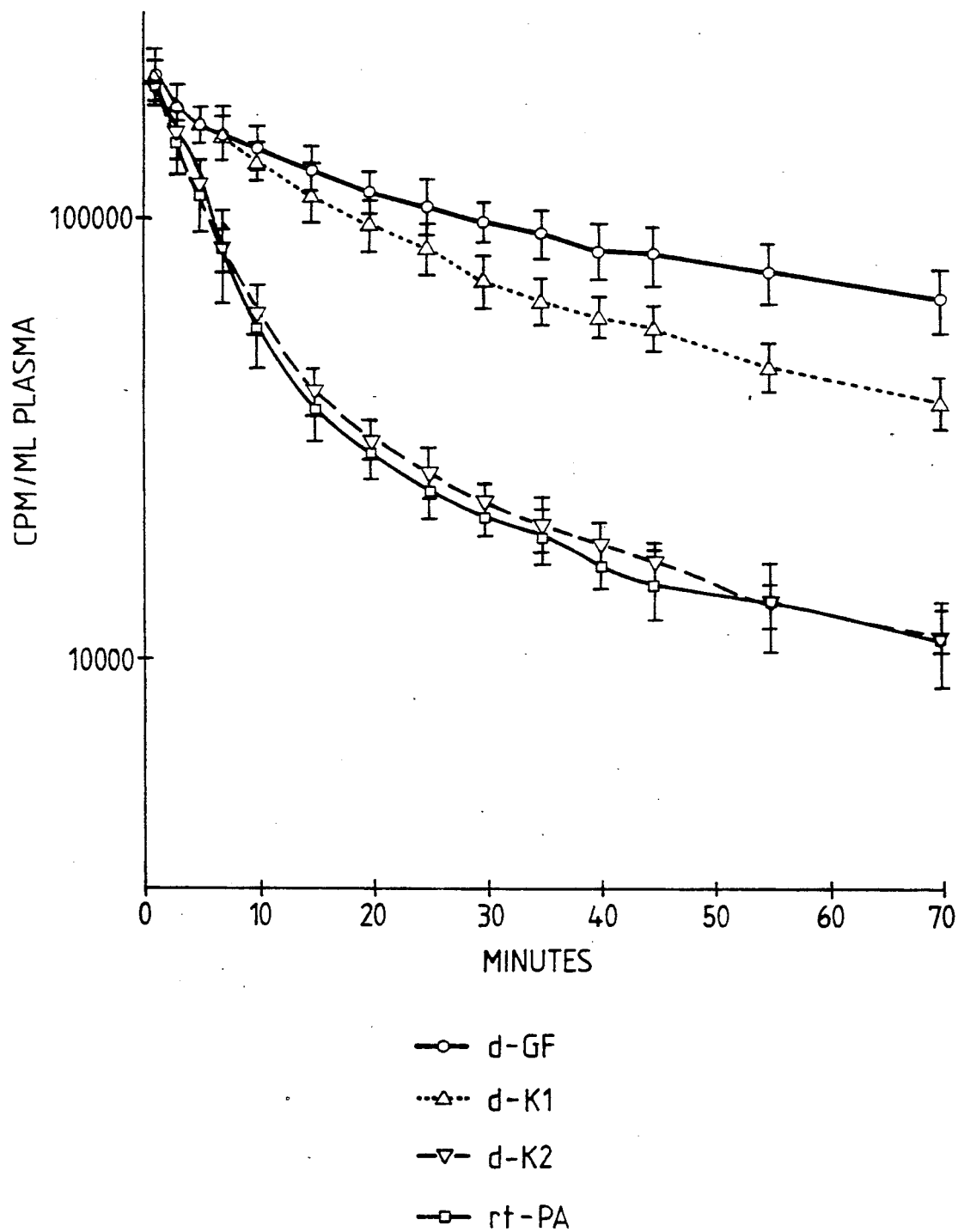
FIG. 10 shows the pharmacokinetic profiles, in rabbits, of the various domain deletion mutants: growth factor deletion, des 44-84 ("d-GF"), Kringle 1 deletion, des 92-179("d-K1"); Kringle 2 deletion, des 174-261("d-K2"); and native t-PA ("rt-PA") as a control.
Figure 11:
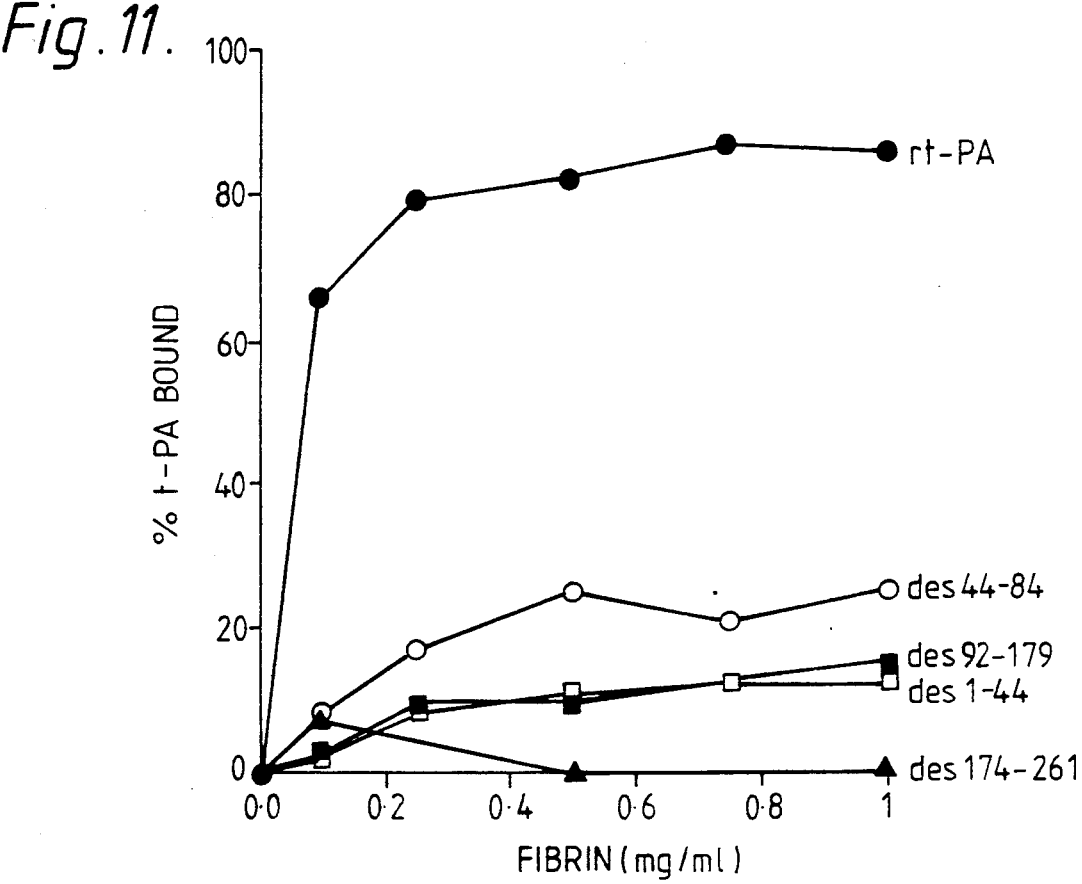
FIG. 11 shows the fibrin binding characteristics of the various domain deletion mutants (see FIG. 10) including finger deletion des 1-44, expressed as percent bound versus fibrin(ogen) concentration.
Figure 15:
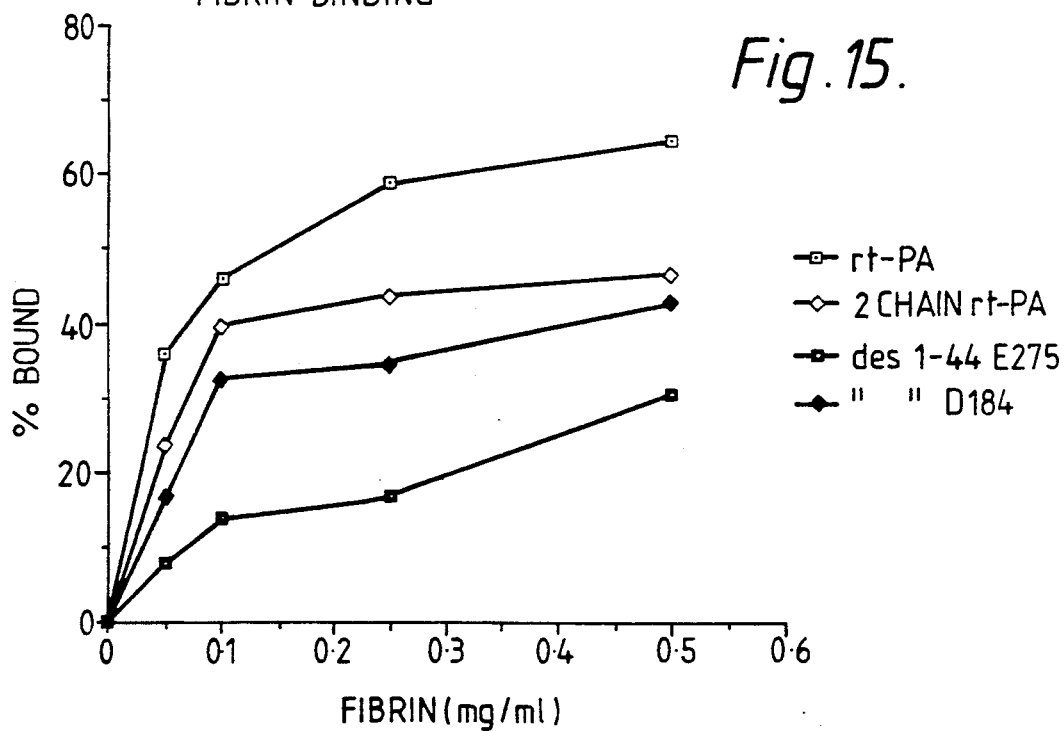
FIG. 15 shows fibrin binding of the following molecules at a t-PA concentration of 100 ng/ml: rt-PA, two-chain native rt. PA, des 1-44E275 and des 1-44D1-84E275. All molecules were produced in stable CHO cell lines.
Figure 16:
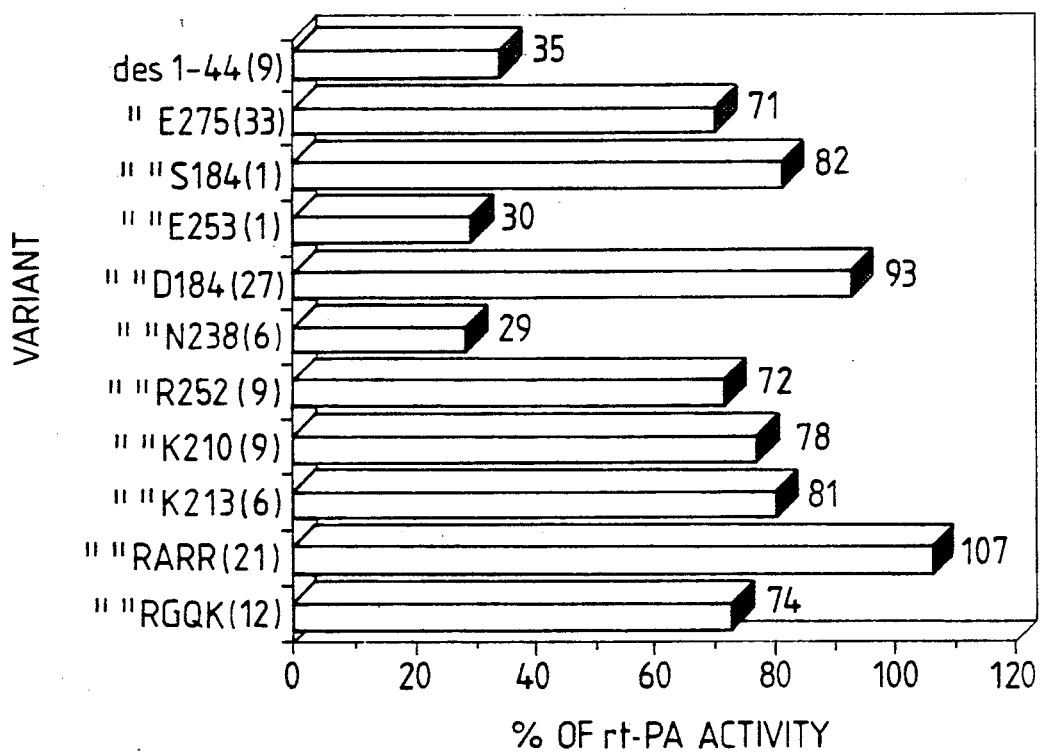
FIG. 16 shows in vitro clot lysis results, expressed as a percent of native specific activity, for the following molecules: des 1-44, des 1-44E275, des 1-44S184,E275, des 1E253E275, des 1-44D184E275, des 1-4N238E275, des 1R252E275, des 1K210E275, des 1-44K213E275, des 1-44R210A211R212R213E275, des 1-44R210Q211Q212K2123E275. Results show averages of several independent observations (number of times in parentheses). (All except des 1-44 were from material expressed transiently in 293 cells and quantified by ELISA.)
Figure 17:
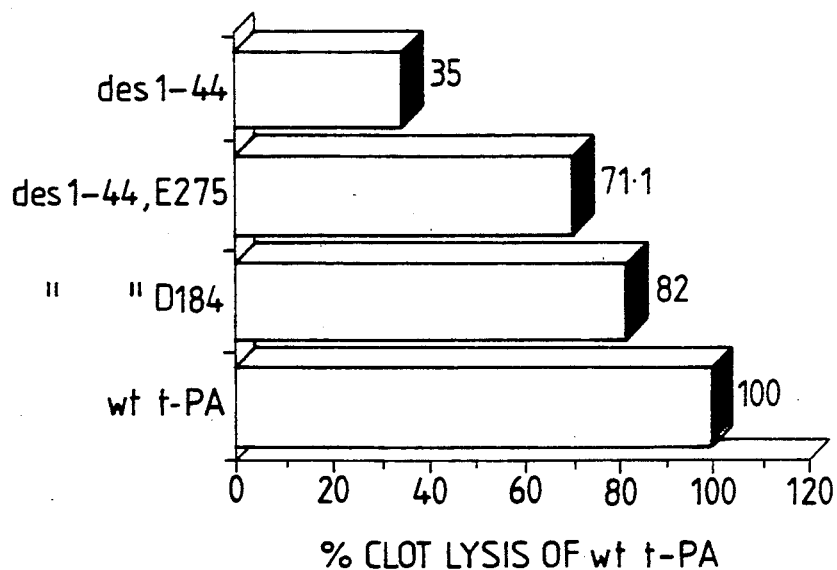
FIG. 17 shows in vitro clot lysis results, expressed as a percent of native specific activity, for the following molecules: rt-PA, des 1-44, des 1-44E275, des 1-44D1-84E275. (All molecules were produced in stable CHO cell lines.

Plasmid p1060 was digested with BglII (partial) and ApaI, and the 8.0 kb fragment was purified by agarose gel electrophoresis and electroelution. Plasmid p1154 was similarly digested with BglII and ApaI and the 1.3 kb fragment isolated. These two fragments were joined using T4 DNA ligase and rATP to produce the plasmid p1179. See FIG. 8. Plasmid p1179 contained the des (1–44)/Glu 275 t-PA mutant (des 1–44E275 t-PA) under the control of the CMV promoter, as well as the β-lactamase gene, the DHFR gene, and the f1 origin of DNA replication. The sequence of the des 1–44E275 t-PA coding region is shown in FIG. 9.

2. Mutagenesis Examples a. Template Preparation

Plasmid p1179 was introduced into E. coli strain JM101 (ATCC No. 33876) via CaCl$_2$-mediated transformation. These cells were then infected with the helper virus M13K07 and single-stranded p1179 DNA was prepared as described by Veira et al., Meth Enzymol. 153, 3 (1987). Briefly, to 0.3 ml of a saturated culture of transformed cells in 2YT broth was added $10^9$–$10^{10}$ pfu of M13K07 and the mixture incubated for 15 min at 37 C. 1.5 ml of fresh 2YT broth, containing 50 μg/ml carbenicillin, was added and the culture was gently shaken for 16 hrs at 37° C. After pelleting the cells, phage and packaged plasmid DNA were harvested and single-stranded DNA prepared as described by Anderson, Nucl. Acids, Res. 9, 3015 (1981).

b. Site-directed in vitro Mutazenesis

Mutagenesis on p1179 was carried out using oligodeoxyribonucleotides essentially as described by Zoller et al., Meth. Enzymol. 100, 468 (1983). except mutants were identified by colony hybridization rather than plaque hybridization. Mutations were verified by DNA sequencing directly on the single. stranded plasmid DNA using the dideoxynucleotide chain termination method (Sanger et al. *Proc. Natl. Acad. Sci. (USA)* 74, 5463 (1977)).

c. Plasmids, Mutants and Primers

Using the methods described above (see, particularly, Part 2b.), the following plasmids were obtained (left column) containing the modifications noted (center column) using the primers shown (right column).

| Plasmid | Mutant | Primer (5' → 3') |
|---|---|---|
| p1184 | Val 213 → Lys | CTGATAGGCAAG<u>AA</u>GTACACAGC |
| p1185 | Ile 210 → Lys | TCCATGATCCTG<u>AA</u>GGGCAAGGTT |
| p1186 | Thr 252 → Arg | AACCGCAGGCTG<u>AGG</u>TGGGAGTA |
| p1188 | Asn 184 → Ser | TGCTACTTTGGG<u>AGC</u>GGGTCAGCC |
| p1189 | Asn 184 → Asp | TGCTACTTTGGG<u>GAC</u>GGGTCAGCC |
| p1193 | Asp 238 → Asn | AATCCTGATGGG<u>AAC</u>GCCAAGCCC |
| p1194 | Ile—Gly—Lys—Val 210–213 → Arg—Ala—Arg—Arg | TCCATGATCCTG<u>CGTGCCCGACGAT</u>ACACAGCA |
| p1224 | Ile—Gly—Lys—Val 210-213 → Arg—Gly—Gln—Lys | TCCATGATCCTG<u>CGTGGCCAGAAGT</u>ACACAGC |
| P1192 | Trp 253 → Glu | CGCAGGCTGACG<u>GAG</u>GAGTACTGT |

3. Expression and Purification a. Plasmid Preparation

Transformed cells were grown to saturation in 500 ml LB broth containing 50 μg/ml carbenicillin. Cells were pelleted by centrifugation and resuspended in 40 ml of 50 ml mM glucose, 10 mM EDTA, 25 mM Tris-HCl (pH 8.0). To this suspension was added 60 ml of 1% sodium dodecyl sulfate, 0.1 M NaOH, and the mixture incubated for 2 min at 25° C., then 10 min at 0° C. To this 52 ml of 4 M acetic acid, 3 M sodium acetate were added and the mixture incubated for min at 0° C. This was then centrifuged at 20,000 rpm for 20 min, the supernatant mixed with 2 volumes of 100% cold ethanol, and the resulting precipitate harvested by centrifugation. The pellet, containing plasmid DNA and RNA, was dried and redissolved in 100 mM Tris (pH 8.0), 10 mM EDTA, 1 μg/ml RNase A. After clarifying by centrifugation, this was adjusted to 0.5 mg/ml in ethidium bromide and an equal weight of CsCl was added. The DNA was then centrifuged in a Beckman VTI65 rotor for 16 hr at 55,000 rpm at 18° C. The DNA band was harvested by side puncture, extracted with n-butanol to remove the ethidium bromide, diluted with H₂O, and precipitated by ethanol. DNA was redissolved in 10 mM Tris (pH 8.0), 1 mM EDTA, to a final concentration of 1 mg/ml.

b. Transfection and Expression 293 cells were grown to confluence. 10 μg of t-PA plasmid DNA (for example, p1179 and its derivatives prepared as described above) were mixed with 1 μg of DNA encoding the VA RNA gene (Thimmappaya et al., *Cell* 31, 543 (1982)) and dissolved in 500 μl of 1 mM Tris-HCl, 0.1 mM EDTA, 0.227 M CaCl₂. Added to this (dropwise while vortexing) was 500 μl of 50 mM HEPES (pH 7.35), 280 mM NaCl, 1.5 mM NaPO4, and the precipitate was allowed to form for 20 min at 25° C. The suspended precipitate was then added to the cells (in 100 mM plate) and allowed to settle for 4 hr in the incubator. The medium was then aspirated off and 2 ml of 20% glycerol in phosphate-buffered saline was added for 30 sec. The cells were washed twice with 10 ml of serum-free medium, then fresh medium was added and the cells incubated for 5 days.

For the creation of stable CHO cell lines expressing the t-PA variants, the BglII/ApaI fragment containing the bulk of the t-PA coding sequences (FIGS. 7 and 8) was ligated to the 6.0 kb BglII/ApaI fragments from the vector pPADHFR-6 (FIG. 3). The resultant plasmids were then introduced into CHO cells and induced to over-express the t-PA variants by amplifying the coding sequence by means of selection in methotrexate-containing media.

c. Purification

Purification of the t-PA products was accomplished by passing the conditioned medium over a column (1 ml bed volume) of controlled glass beads to which an anti-t-PA goat polyclonal A6 antibody (prepared according to standard methods known per se) had been coupled. Before loading the medium, the column was equilibrated with phosphate-buffered saline and, after loading, the column was with 0.1 M Tris-HCl (pH 7.5), 1 M NaCl. The t-PA was eluted with 0.1 M acetic acid, 0.15 M NaCl, 0.02 M arginine (pH 2.0), and fractions were immediately neutralized with Tris-base. Fractions were adjusted to 0.01% Tween 80 before pooling. In some cases, t-PA variants were prepurified on lysine-sepharose prior to final purification on an anti-t-PA goat polyclonal antibody column.

D. Biological and Pharmacokinetic Assays

1. t-PA Quantitation

Protein concentrations were routinely determined by an ELISA standardized to native sequence t-PA (see EPA 93619, supra.). Protein purity and homogeneity were analyzed by polyacrylamide gel electrophoresis in the presence of sodium dodecyl sulfate (PAGE-SDS) with the buffer system of Laemmli, *Nature* 227, 680 (1970). Typically, 7 to 17% gradient gels were used and proteins were visualized with the silver-staining technique of Morrissey, *Anal. Biochem.* 117. 307 (1981).

2. Clot Lysis

The t-PA variants were assayed for their ability to lyse fibrin in the presence of saturating concentrations of plasminogen, according to the method of (Carlsen et al., *Anal. Biochem.* 168, 428 (1988)). The in vitro clot lysis assay measures the activity of tissue plasminogen activators by turbidimetry using a microcentrifugal analyzer. A mixture of thrombin and t-PA test samples are centrifuged into a mixture of fibrinogen and plasminogen to initiate clot formation and subsequent clot dissolution. The resultant profile of absorbance versus time is analyzed to determine the assay endpoint. Activities of the t-PA variants were compared to a standard curve of rt-PA (EPA 093619, supra.). The buffer used throughout the assay was 0.06 M sodium phosphate, pH 7.4 containing 0.01% (v/v) Tween 80 and 0.01% (w/v) sodium azide. Human thrombin was at a concentration of 33 units/ml. Fibrinogen (at 2.0 mg/ml clottable protein) was chilled on wet ice to precipitate fibronectin and then gravity filtered. Glu-plasminogen was at a concentration of 1 mg/ml. The analyzer chamber temperature is set at 37° C. The loader is set to dispense 20 $\mu$l of rt-PA ($-500$ ng/ml to 1.5 $\mu$g/ml) as the sample for the standard curve, or 20 $\mu$l of variant rt-PAs at a concentration to cause lysis within the range of the standard curve. 20 $\mu$l of thrombin as the secondary reagent, and 200 $\mu$l of a 50:1 (v/v) fibrinogen: plasminogen mixture as the primary reagent. The absorbance/time program was used with a 5 min incubation time, 340-nm-filter and a 90 interval readings.

3. Fibrin Binding

The method for fibrin binding is a modification of the method described by Rijken et al., *J. Biol. Chem.* 257, 2920 (1982). The t-PA sample to be tested is added to a solution containing 0.05 M Tris (pH 7.4), 0.12 M NaCl, 0.01% Tween 80, 1 mg/ml human serum albumin, and various concentrations of plasminogen-free fibrin (0, 0.05, 0.1, 0.25 and 0.5 mg/ml). The final volume of the reaction mixture was 1 ml. The sample was incubated at 37° C. for 5 min, followed by the addition of 1 unit of thrombin. The samples were then incubated for 1 hr at 37° C. The clot was removed by centrifugation, and the amount of t-PA remaining unbound in the supernatant was determined by ELISA. The data is plotted as percent t-PA variant bound versus the fibrin(ogen) concentrations.

4. Pharmacokinetics a. Objective

To compare the terminal half-lives and clearances of $^{125}$I-labeled rt-PA and t-PA mutants.

b. Procedure

Twenty rabbits were assigned randomly to one of four treatment groups: rt-PA, des 1–44 t-PA, des 1–44E275 t-PA and des 1–44D184E275 t-PA. The proteins were labeled with $^{125}$I to approximately 10 $\mu$Ci/kg and mixed with 0.1 mg/kg rt-PA to decrease nonspecific adsorption of the labeled protein. The dose of TCA precipitable $^{125}$I-protein was nominally 5 $\mu$Ci/kg.

The rabbits had a catheter with a heparin lock in each ear. The dose was administered as an IV bolus in one catheter, followed by a saline flush. All blood samples were obtained from the opposite ear. One ml blood samples were obtained at the following times: 0 (before the dose) and 2, 5, 15, 30, 45, 60, 75, 90, 120, 150, and 180 minutes after the dose. Saline was used to flush the catheters and replace blood volume at each time point. The blood samples were put into 1.5 ml Eppendorf tubes containing 4.2 mM EDTA and 1 mM PPACK. The tubes were maintained on ice until centrifuged. After centrifugation, the plasma was removed immediately, placed in Eppendorf tubes, and stored on ice until the end of the study. Proteins in 100 $\mu$l of each plasma sample were precipitated with trichloracetic acid. The $^{125}$I that was bound to proteins was quantified by counting the gamma emissions of each precipitate. The results were based on CPM/100 $\mu$l of sample and converted to CPM/ml for data analysis.

c. Data Analysis

The area-under-the-curve (AUC) for each rabbit was computed from 2 to 180 minutes by the trapezoid method using the AUC procedure. Clearance was calculated from the formula CL=Dose/AUC. The clearance of each protein in relation to rt-PA appears below:

| Comparison | Ratio of Clearances |
| --- | --- |
| des 1–44 t-PA | 0.12 |
| des 1–44E275 t-PA | 0.11 |
| des 1–44D184E275 t-PA | 0.38 | d. Summary

The ranking of terminal half-lives for the $^{125}$I-labeled proteins is as follows: rt-PA, des 1–44 t-PA, des 1–4-4E275 t-PA, des 1–44D184E275 t-PA. The actual half-life values must be determined from pharmacokinetic studies with unlabeled proteins. The clearance of $^{125}$I-labeled des 1–44 t-PA and des 1–44E275 t-PA were comparable and approximately one-ninth of the value obtained for $^{125}$I-labeled rt-PA. The clearance of the triple mutant, des 1–44D184E275 t-PA, was three times higher than the other mutants and approximately 2.5 times lower than the $^{125}$-labeled rt-PA.

E. Pharmaceutical Compositions

The compounds of the present invention can be formulated according to known methods to prepare pharmaceutically useful compositions, whereby the human tissue-type plasminogen activator product hereof is combined in admixture with a pharmaceutically acceptable carrier vehicle. Suitable vehicles and their formulation, inclusive of other human proteins, e.g., human serum albumin, are described for examples in Remington's *Pharmaceutical Sciences* by E. W. Martin, which is hereby incorporated by reference. Such compositions will contain an effective amount of the protein hereof together with suitable amount of vehicle in order to prepare pharmaceutically acceptable compositions suitable for effective administration to the host.

For example, the human tissue-type plasminogen activator hereof may be parenterally administered to subjects suffering from cardiovascular diseases or conditions. Dosage and dose rate may be parallel that currently in use in clinical investigations of other cardiovascular, thrombolytic agents, e.g. about 1–2 mg/kg body weight as an intravenous or intra-arterial dose over 1.5–12 hours in patients suffering from myocardial infarction, pulmonary embolism, etc.

As one example of an appropriate dosage form, a vial containing 50 mg human tissue-type plasminogen activator, arginine, phosphoric acid and polysorbate 80 may be reconstituted with 50 ml sterile water for injection and mixed with a suitable volume of 0.9 percent Sodium Chloride Injection.

The extended or reduced half-life human tissue-type plasminogen activator may be suitable for rapid i.v. injection, particularly as a bolus, for example. This would eliminate the need for complex administration procedures and may increase the opportunity for the use of t-PA in settings with limited medical equipment such as in emergency vehicles staffed with paramedic personnel. An extended half-life of human tissue-type plasminogen activator may also lower, safer initial doses and could maintain thrombolytically effective plasmin levels for up to 45 minutes or longer. A longer half-life of human tissue-type plasminogen activator may also be useful for low dose extended therapy which may be necessary to avoid reocclusion following successful acute thrombolysis or for extended thrombolysis which may be necessary in cases of peripheral vascular occlusion. A reduced half-life of human tissue-type plasminogen activator may in certain patients be the desired type of thrombolytic therapy by providing effective plasmin levels over a shortened period of time.

What is claimed is:

1. A human tissue plasminogen activator (t-PA) comprising the structure des 1–44R210A211R212R213E275 t-PA or des 1–44R252E275 t-PA.

2. A human tissue plasminogen activator according to claim 1 which is des 1–44R210A211R212R213E275 t-PA.

3. A human tissue plasminogen activator according to claim 1 which is des 1–44R252E275 t-PA.

* * * * *

UNITED STATES PATENT AND TRADEMARK OFFICE
CERTIFICATE OF CORRECTION

PATENT NO. : 5,094,953  
DATED : 10 March 1992  
INVENTOR(S) : ANDERSON, et al.

It is certified that error appears in the above-identified patent and that said Letters Patent is hereby corrected as shown below:

Column 3, line 59, after "region," insert --except for the surprising discovery that such altered species have--.

Column 5, line 58, replace "1.44" with --1-44--.

Column 7, line 54 replace, "1D184E275" with --1-44D184E275--.

Column 7, line 61, replace, "1-4K213E275" with --1-44K213E275--.

Column 7, line 62, replace, "1R252E275" with --1-44R252E275--.

Column 8, line 14, replace 1E253E275" with -- 1-44E253E275-- and replace "1-4N238E275" with --1-44N238E275--.

Column 8, line 15, replace "1R252E275" with --1-44R252E275-- and replace "1K210E275" with --1-44K210E275--.

Column 10, line 31, replace "trol" with --trpl--.

Column 11, line 59, replace "CHO.K1" with --CHO-K1--.

Column 12, line 11, after "of" insert --transfection is calcium treatment using calcium as described by--.

UNITED STATES PATENT AND TRADEMARK OFFICE
CERTIFICATE OF CORRECTION

PATENT NO. : 5,094,953
DATED     : 10 March 1992
INVENTOR(S) : ANDERSON, et al.

It is certified that error appears in the above-identified patent and that said Letters Patent is hereby corrected as shown below:

Column 12, line 35, before "percent" insert --6--.

Column 12, line 45, please place a period (.) between "mutation" and "Mutants".

Column 13, line 18, replace "174.261" with --174-261--.

Column 13, line 56, replace "GRL" with --CRL--.

Column 14, line 65, replace "NaCl.0.5" with --NaCl-0.5"--.

Column 15, line 24, replace "pPA.N44intA" with --pPA-N44intA--.

Column 16, line 24, after "37" insert --°--.

Column 16, line 30, replace "24.mer" with --24-mer--.

Column 19, line 25, replace "ClaI.SalI" with --ClaI-SalI-.

Column 19, line 38, after "labeled" delete "co".

Column 19, line 40, replace "ClaI.KpnI" with --ClaI-KpnI-.

Column 19, line 41, replace "ClaI.KpnI" with --ClaI-KpnI-.

Column 20, line 21, replace "AKpn" with --ΔKpn--.

UNITED STATES PATENT AND TRADEMARK OFFICE
CERTIFICATE OF CORRECTION

PATENT NO. : 5,094,953
DATED : March 10, 1992
INVENTOR(S) : Anderson, et al

It is certified that error appears in the above-indentified patent and that said Letters Patent is hereby corrected as shown below:

Column 21, line 41 between "for" and "min" insert --30--.

Column 21, line 66 replace "NaPO4" with --$NaPO_4$--.

Signed and Sealed this

Fourteenth Day of September, 1993

Attest:

BRUCE LEHMAN

*Attesting Officer*      *Commissioner of Patents and Trademarks*